(12) United States Patent
Boussemart-Prouvost et al.

(10) Patent No.: US 9,603,914 B2
(45) Date of Patent: Mar. 28, 2017

(54) **MUTANT STRAINS OF *NEOSPORA* AND USES THEREOF**

(71) Applicant: VITAMFERO, Tours (FR)

(72) Inventors: Anne-France Boussemart-Prouvost, Tours (FR); Pascal Breton, Tours (FR); Mauld Lamarque, Tours (FR); Solen Morisse-Philippe, Tours (FR); Edouard Seche, Tours (FR)

(73) Assignee: VITAMFERO, Tours (FR)

( * ) Notice: Subject to any disclaimer, the term of this patent is extended or adjusted under 35 U.S.C. 154(b) by 0 days.

(21) Appl. No.: 14/419,055

(22) PCT Filed: Aug. 2, 2013

(86) PCT No.: PCT/FR2013/051877
§ 371 (c)(1),
(2) Date: Feb. 23, 2015

(87) PCT Pub. No.: WO2014/020291
PCT Pub. Date: Feb. 6, 2014

(65) Prior Publication Data
US 2015/0190487 A1   Jul. 9, 2015

(30) Foreign Application Priority Data
Aug. 2, 2012   (FR) ..................... 12 57544

(51) Int. Cl.
| | | |
|---|---|---|
| *A61K 39/012* | (2006.01) |
| *A61K 39/002* | (2006.01) |
| *C07K 14/44* | (2006.01) |
| *C12N 1/10* | (2006.01) |
| *C12Q 1/68* | (2006.01) |
| *A61K 39/00* | (2006.01) |

(52) U.S. Cl.
CPC ............ *A61K 39/002* (2013.01); *C07K 14/44* (2013.01); *C12N 1/10* (2013.01); *C12Q 1/6893* (2013.01); *A61K 2039/522* (2013.01); *A61K 2039/575* (2013.01); *C12Q 2600/158* (2013.01)

(58) Field of Classification Search
None
See application file for complete search history.

(56) References Cited

U.S. PATENT DOCUMENTS

2009/0053266 A1   2/2009   Dubremetz et al.

FOREIGN PATENT DOCUMENTS

| | | |
|---|---|---|
| EP | 0 953 641 A2 | 11/1999 |
| WO | 2005/072754 A1 | 8/2005 |

OTHER PUBLICATIONS

Diana Marcela Penarete-Vargas et al.:"Protection against Lethal Neospora caninum Infection in Mice Induced by Heterologous Vaccination with amicl mic3 Knockout Toxoplasma gondii Strain", Infection and Immunity, American Society for Microbiology. US, vol. 78. No. 2. Feb. 2010 (Feb. 2010), pp. 651-660, XP002696799, ISSN: 0019-9567. 001: 10.1128/IAI.00703-09 [retrieved on Dec. 7, 2009] The whole document.

A. Naguleswaran et al.: "Neospora caninum Microneme Protein NcMIC3: Secretion, Subcellular Localization. and Functional Involvement in Host Cell Interaction", Infection and Immunity, vol. 69. No. 10. Oct. 2001 (Oct. 2001), pp. 6483-6494. XP055061688, ISSN: 0019-9567. 001: 10.1128/IAI.69.10.6483-6494.2001 the whole document.

International Search Report, dated Jan. 30, 2014, from corresponding PCT application.

*Primary Examiner* — Brian J Gangle

(74) *Attorney, Agent, or Firm* — Young & Thompson

(57) ABSTRACT

A mutant strain of *Neospora* spp, in which the function of the NcMIC3 protein and/or the function of the NcMIC1 protein is suppressed, and uses thereof in a pharmaceutical composition or in a vaccine composition.

4 Claims, 14 Drawing Sheets

Figure 1:
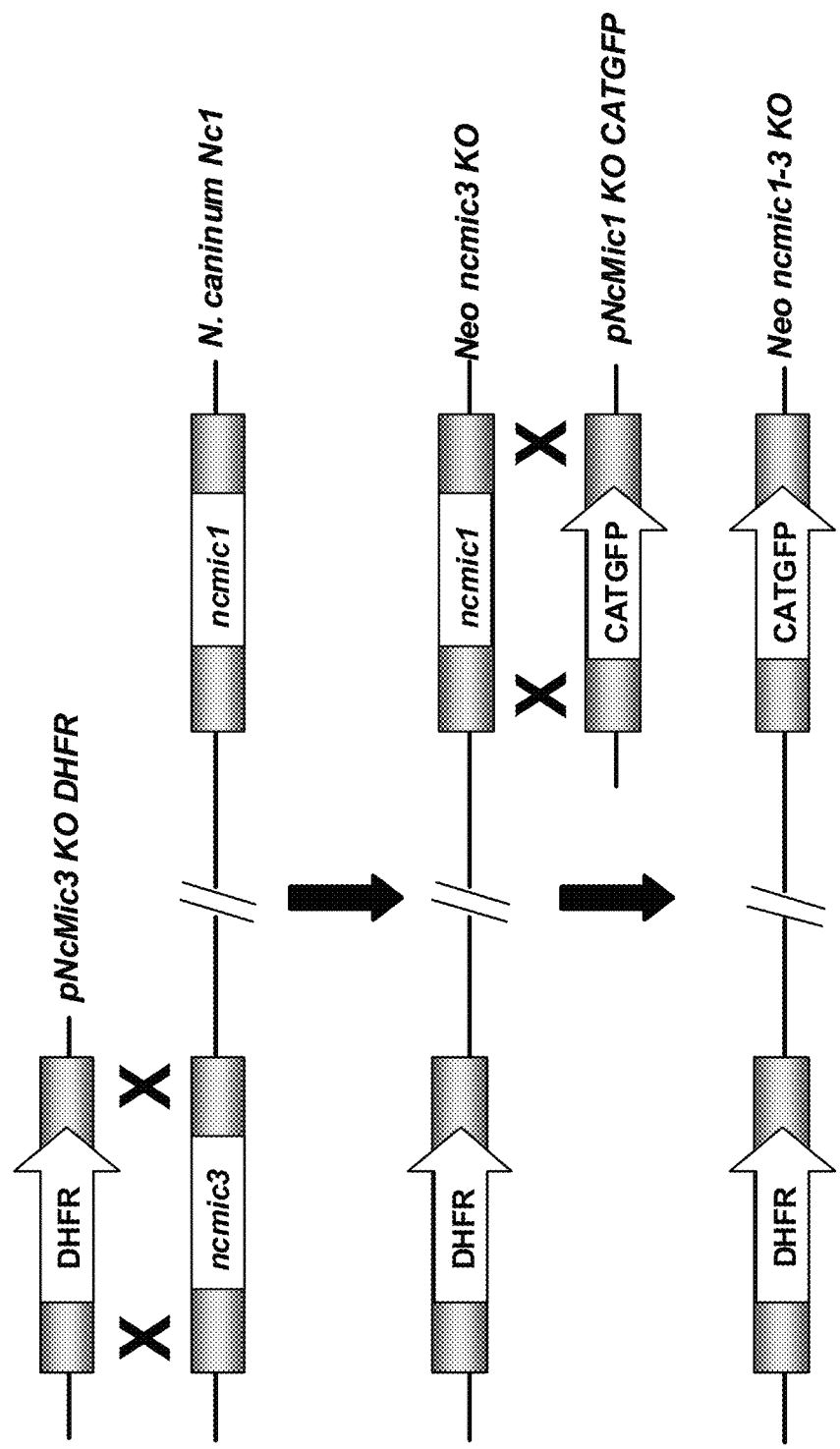

FIGURE 2-A
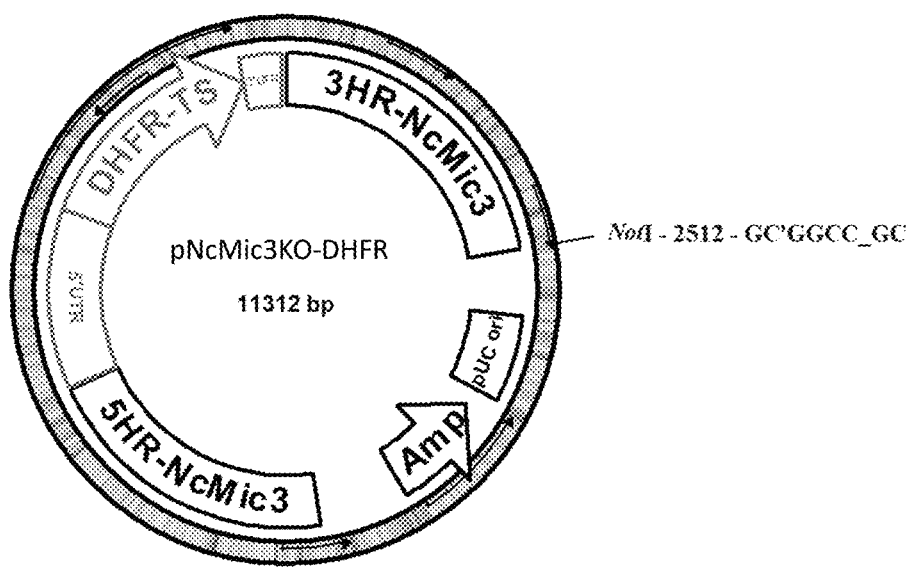
FIGURE 2-B
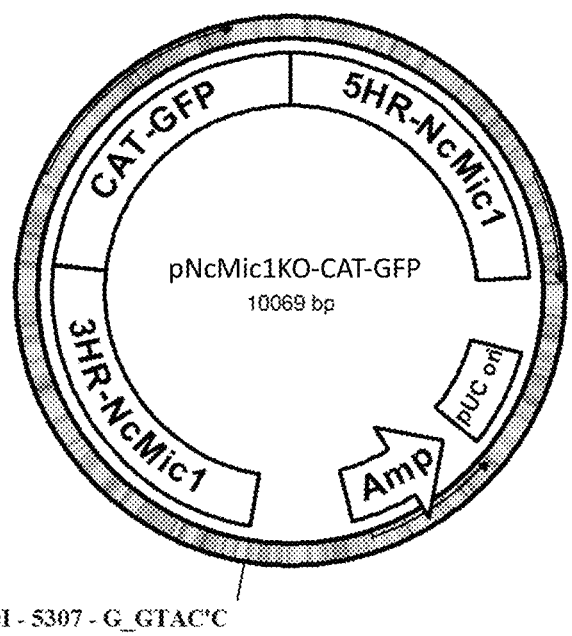

FIGURE 3-A
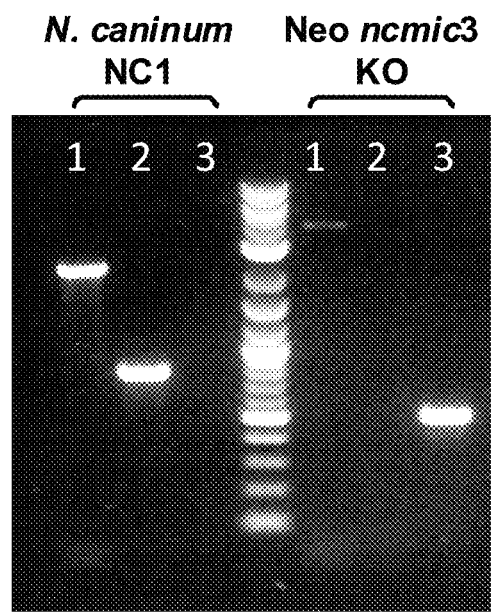
FIGURE 3-B
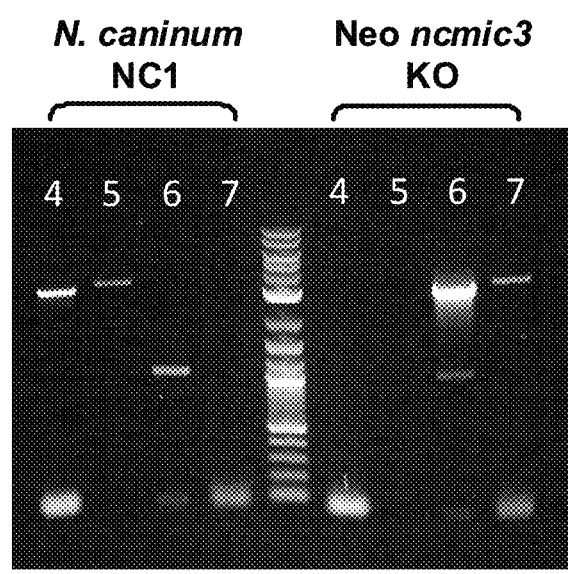

FIGURE 4-A
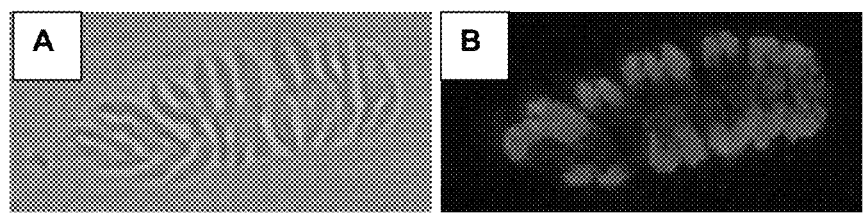
FIGURE 4-B
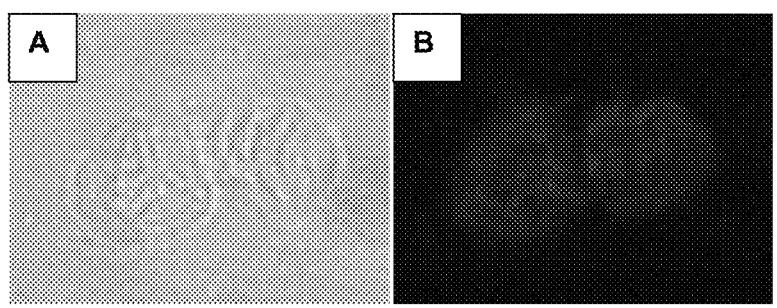

FIGURE 12-A
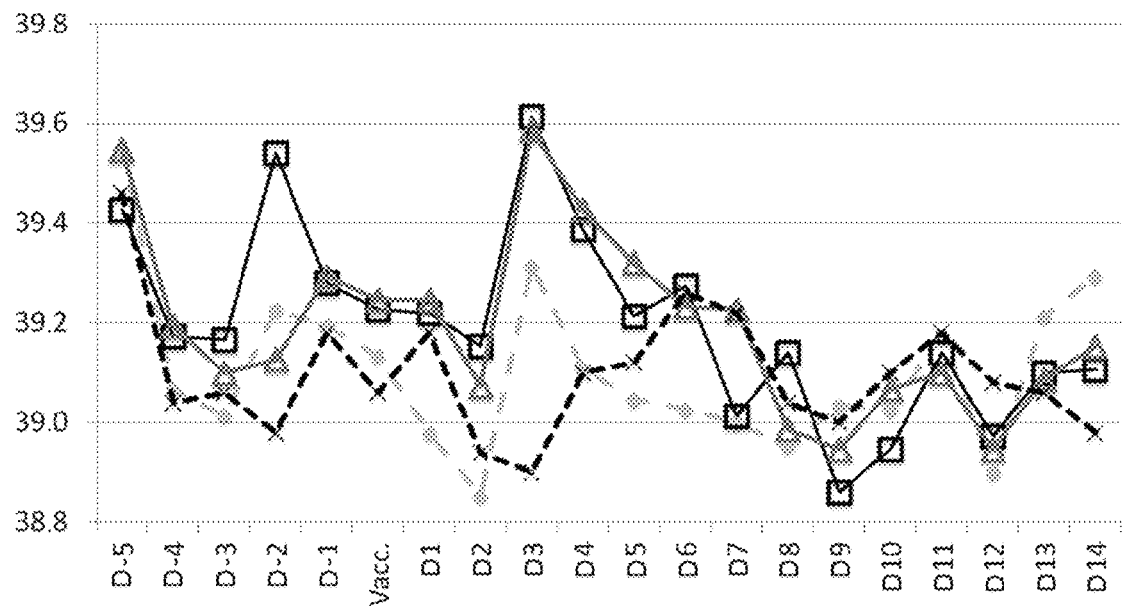
FIGURE 12-B
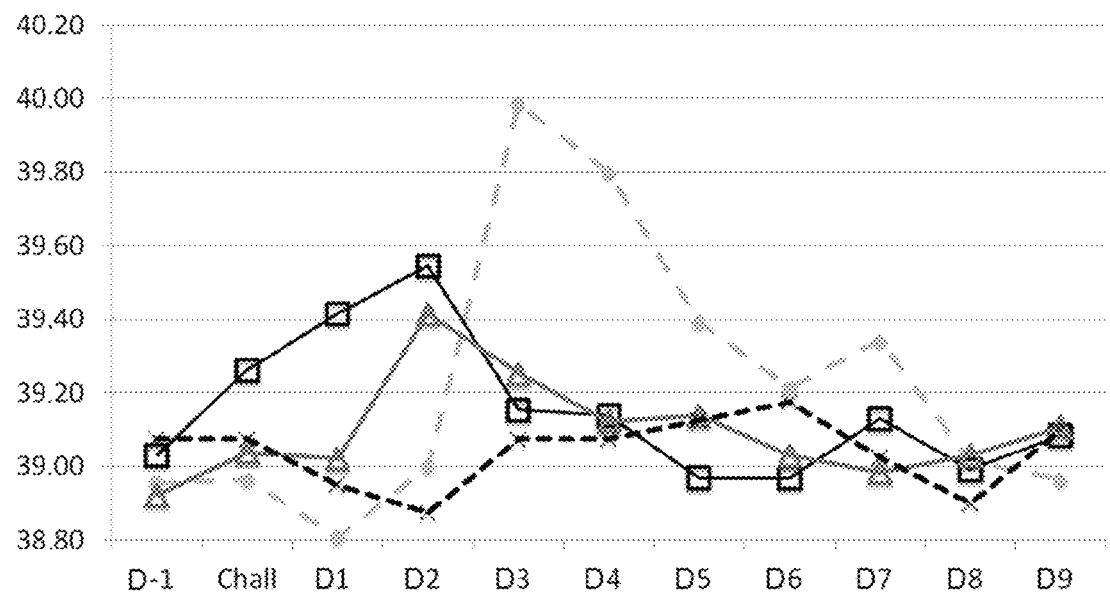

FIGURE 14
*Neospora caninum*
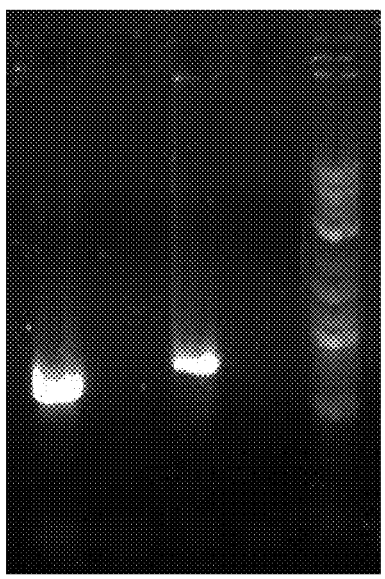
*Neo Mic1-3 KO*
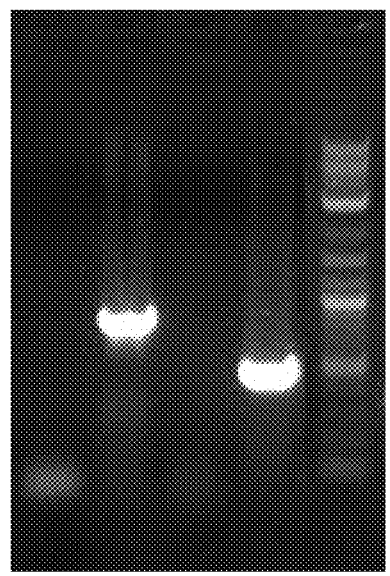

MUTANT STRAINS OF *NEOSPORA* AND USES THEREOF

The present invention relates to a mutant strain of *Neospora* spp, the use thereof in a pharmaceutical composition and the use thereof in a vaccine composition.

*Neospora caninum* is an intracellular parasite, responsible for neosporosis. It belongs to the phylum of the Apicomplexans (a branch of the Apicomplexa) which includes a large number of predominantly intracellular parasites. These parasites are responsible for diseases such as neosporosis, toxoplasmosis, malaria, coccidiosis and cryptosporidiosis. They have in common a specific process for the invasion of host cells in several steps, leading to the formation of a parasitophorous vacuole in which the parasite develops.

The life cycle of *Neospora caninum* has two distinct phases: an asexual phase in an intermediate host such as the mouse, ovines and bovines which leads to the production of tachyzoites and then cysts containing bradyzoites, and a sexual phase in the definitive host (mainly the dog) which leads to the production of oocysts, containing sporozoites, which are eliminated in the faeces.

Animal neosporosis is an significant economic problem in the area of livestock farming and in particular in cattle rearing, where it causes a decrease in the weight gain of calves, a decrease in fertility, a decrease in milk production but in particular is recognized as being one of the major causes of abortions. Thus, every year throughout the world, 30 to 40 million abortions are caused by *Neospora caninum* in the bovine population. In contrast to *Toxoplasma gondii*, the maternal-foetal transmission of the parasite and the congenital infection of the foetus occur not only in the case of primary infection during gestation but also in cows chronically infected prior to gestation.

The contamination of cattle may occur by two quite distinct routes:
 By horizontal contamination, i.e. by ingestion of feed contaminated with oocysts excreted by a definitive host. In the case of gestation, the risk of abortion is then 80%.
 By vertical contamination, i.e. by maternal-foetal transmission of the parasite from the mother to her calves. A cow infected prior to gestation may, during subsequent gestations, either abort again, or give birth to a healthy calf, or, most often, transmit the parasite to its calf. This calf will be infected by *Neospora caninum* and, if it is a female, it will in its turn have an increased risk of transmitting the parasite to its offspring with the possibility of abortion.

These consequences obviously have important economic repercussions for livestock farms. Thus, neosporosis is responsible for a loss of € 35 million per 1.2 million dairy cows in California (Dubey, *J. Am. Vet. Med. Assoc.*, 1999, Apr. 15; 214(8): 1160-3), of € 19 million per 1.6 million cows in the Netherlands (Bartels et al., *Vet. Parasitol.*, 2006, Apr. 15; 137(1-2): 17-27) and of € 10 million per 0.7 million cows in Switzerland (Häsler et al., *Prev. Vet. Med.*, 2006, Dec. 18; 77(3-4): 230-53).

The development of a vaccine is a major objective for combating neosporosis. Several strategies for constructing a vaccine against neosporosis are currently under investigation:
 Vaccines based on parasites inactivated by irradiation, heat, etc. These vaccines generate a protective immune response but generally require the presence of adjuvants as well as a great many booster vaccinations. Currently, a single vaccine directed against bovine neosporosis is marketed in certain geographical regions and in particular in the United States. This is the vaccine NeoGuard® marketed by the company Intervet. This vaccine is constituted by inactivated tachyzoites of *Neospora caninum* and a particular adjuvant (Havlogene). The efficacy of the vaccine NeoGuard®, of about 50%, is regarded as partial. Moreover, the method of administration of this vaccine requires two injections spaced a few weeks apart during the first year of vaccination and then one or two injections in subsequent years.
 Vaccines based on attenuated live parasites; these strains are generally obtained either in vitro by successive passes of the parasite in culture in host cells in the presence or absence of mutagenic agents, or by the isolation of less virulent strains in nature, or by other methods such as irradiation. These vaccines are generally very effective but have the major drawback that they have not been characterized on a molecular level and reversion to a virulent form is always to be feared. Several isolates such as Nc-Nowra (Miller et al., *Aust. Vet. J.*, 2002, October; 80(10): 620-5) and Nc-Spain-1H (Regidor-Cerrillo et al., *Parasitology*, 2008, December; 135(14): 1651-9) have been isolated from calves infected asymptomatically. The vaccine potential of these attenuated strains is currently being evaluated.
 Recombinant vaccines: a cowpox virus expressing the NcSRS2 antigen of *N. caninum* was evaluated in vaccination experiments in the mouse (Nishikawa et al., *Parasitol. Res.*, 2000, November; 86(11): 934-9; Nishikawa et al., *Vaccine*, 2001, Jan. 8; 19(11-12): 1381-90) and demonstrated its capacity for inducing a protective immune response in the mouse. More recently, a strain of *Brucella abortus* was used for expressing different antigens of *N. caninum* (Ramamoorthy et al., *Int. J. Parasitol.*, 2007, November; 37(13): 1531-8 and Ramamoorthy et al., *Int J Parasitol.*, 2007 November; 37(13): 1521-9). The strains expressing the NcMIC1 protein or the NcGRA6 protein effectively protect the mice from infection with *N. caninum* but raise the problems of using a strain that is pathogenic in bovines.
 Subunit vaccines composed of proteins originating from parasites capable of inducing a protective immune response. These vaccines generally require the presence not only of adjuvants but also require numerous booster vaccinations and are generally less effective in terms of immune response induced in the vaccinated individual. Several vaccination tests have been undertaken with different antigenic proteins. Thus, inoculation with the NcSRS2 protein in mice blocks maternal-foetal transmission (Haldorson et al., *Int. J. Parasitol.*, 2005, November; 35(13): 1407-15) and, combined with Freund's adjuvant, induces an immune response similar to the immune response generated by the inoculation with live *N. caninum* tachyzoites (Staska et al., *Infect. Immune.*, 2005, March; 73(3): 1321-9). Vaccination tests have also been conducted in mice with the NcMIC1 or NcMIC3 protein and have demonstrated a prevention of cerebral infections after an infectious challenge (Cannas et al., *J. Parasitol.*, 2003, February; 89(1): 44-50; Allaedine et al., *J. Parasitol.*, 2005, June; 91(3): 657-65). It has also been demonstrated that mouse antibodies immunized with the Nc-AMA1 protein significantly reduced cellular infection of *N. caninum*.

Despite the serious economic consequences in cattle rearing, no vaccine that is effective, safe and simple to use vaccine is currently marketed or in the development phase. There is consequently a real need to make a vaccine available that is both effective against neosporosis, easy to use and displays excellent safety.

Surprisingly, the inventors found that the suppression of the function of the NMIC3 protein alone, or the suppression of the function of the two NMIC3 and NMIC1 proteins, in a strain of *Neospora caninum*, leads to a mutant strain that has infectious and immunogenic properties, conferring on mammals a vaccine protection against the harmful effects of neosporosis.

The present invention therefore relates to a mutant strain of *Neospora* spp in which the function of the NMIC3 protein and/or the function of the NMIC1 protein is suppressed.

The present invention therefore also relates to a mutant strain of *Neospora* spp in which the function of the NMIC3 protein is suppressed, in particular by the inhibition of the expression of the nmic3 gene, and/or the function of the NMIC1 protein is suppressed, in particular by the inhibition of the expression of the nmic1 gene.

The present invention therefore relates to a mutant strain of *Neospora* spp in which the function of the NMIC3 protein is suppressed.

The present invention therefore relates to a mutant strain of *Neospora* spp in which the function of the NMIC1 protein is suppressed.

The present invention therefore relates to a mutant strain of *Neospora* spp in which the function of the protein NMIC3 and optionally the function of the NMIC1 protein are suppressed.

The present invention therefore relates to a mutant strain of *Neospora* spp in which the function of the NMIC3 protein is suppressed, in particular by the inhibition of the expression of the nmic3 gene, and optionally the function of the NMIC1 protein is suppressed, in particular by the inhibition of the expression of the nmic1 gene.

Proteins are the effectors of cellular activity. The suppression of the function of a protein may result from its absence from biosynthesis or from its non-functionality. The origin of this dysfunction may be linked to disturbances occurring during transcription of the gene encoding the protein, during its translation or may occur during the process of maturation of the protein (post-translational modifications). The deletion of the gene also explains why no protein can be synthesized.

The NMIC1 and NMIC3 proteins are proteins of the micronemes, secretory organelles of the apicomplexans which play a central role in the recognition and the adhesion to the host cells. In *Neospora caninum*, the NcMIC1 protein is a protein of 460 amino acids encoded by the ncmic1 gene, which comprises 4 exons. The polypeptide sequence of NcMIC1 contains a signal peptide of 20 amino acids followed by two repeat regions (48 amino acids and 44 amino acids) in tandem (Keller et al., *Infect Immune*. 2002 June; 70(6): 3187-98).

The NcMIC3 protein of *Neospora caninum* is encoded by the ncmic3 gene, which comprises a single exon. This protein has 362 amino acids.

The inventors have constructed a mutant strain of *Neospora caninum* called Neo ncmic1-3 KO, in which the function of the NcMIC1 protein and the function of the NcMIC3 protein have been suppressed, a mutant strain Neo ncmic3 KO, in which only the function of the NcMIC3 protein has been suppressed, and a mutant strain Neo ncmic1 KO, in which only the function of the NcMIC1 protein has been suppressed. These three mutant strains of *Neospora caninum* are the first example of attenuated live strains of *Neospora caninum* obtained by the controlled and targeted deletion of virulence genes or by the controlled and targeted suppression of the functions of virulence proteins.

In the present invention, by "the function of the NMIC1 protein is suppressed" is meant either the absence of expression of the NMIC1 protein, or is meant the expression of a non-functional NMIC1 protein, for example the expression of a protein not having the function of the NMIC1 protein and having a certain amino acid sequence identity with that of the NMIC1 protein.

By "the function of the NMIC3 protein is suppressed" is meant either the absence of the expression of NMIC3, or the expression of a non-functional NMIC3 protein, for example a protein not having the function of the NMIC3 protein and having a certain amino acid sequence identity with that of the NMIC3 protein.

The absence of the expression of the NMIC1 protein or of the NMIC3 protein may result from the deletion of the whole of the nmic1 or nmic3 gene, or of its coding region, or from a mutation, a deletion or an insertion of one or more nucleotides in the coding region of the nmic1 or nmic3 gene leading to the absence of the expression of the proteins or to proteins with little amino acid sequence identity with the NMIC1 or NMIC3 proteins, or a dysfunction of the promoter region or regulatory region cis or trans of the nmic1 or nmic3 gene, or a dysfunction of one or more transcription factors able to bind to said promoter region, or a dysfunction of the translation of messenger RNA, or some epigenetic modifications that are well known to a person skilled in the art. Thus, by "inhibition of the expression of the nmic1 or nmic3 gene" is meant all the mechanisms that disturb the transcription of the nmic1 or nmic3 gene to messenger RNAs or all the mechanisms that disturb the translation of the messenger RNA to NMIC1 or NMIC3 proteins, these two steps being necessary for the synthesis of a functional NMIC1 or NMIC3 protein.

A non-functional NMIC1 protein or a non-functional NMIC3 protein is a protein that does not have the capacity to recognize the host cells or that does not allow the adhesion of the parasite to said host cells. A non-functional protein may result from a mutation, a deletion or an insertion of one or more nucleotides in the coding region of the nmic1 or nmic3 gene. In this case, the modification of the nucleic acid of the coding region does not block the mechanism of the expression of the protein, which may optionally retain a certain amino acid sequence identity with that of the NMIC1 protein or that of the NMIC3 protein, but changes the reading frame of the corresponding mRNA during translation of the protein. The non-functionality of the NMIC3 protein, or of the NMIC1 protein, may also be the consequence of post-translational modifications that are ineffective or insufficient (i.e. glycosylation, isoprenylation, phosphorylation, sulphation, amidation, acetylation, alkylation, etc.) and which allow it to perform its function.

The function of the NMIC3 protein, or of the NMIC1 protein, may also be suppressed indirectly, in particular by altering or suppressing the expression of one or more other proteins (in particular other adhesins) which bind to the NMIC3 protein, or to the NMIC1 protein, to form a functional complex. The destructuring of such a complex leads to a loss of function of the NMIC3 protein, or of the NMIC1 protein.

In a particular embodiment, the invention relates to a mutant strain of *Neospora* in which only the function of the NMIC3 protein is suppressed.

The inventors found that the suppression of the function of the NcMIC3 protein alone in *Neospora caninum* makes it possible to significantly reduce the virulence of the parasite in vivo. Nevertheless, the double suppression of the function of the NcMIC3 protein and of the function of the NcMIC1 protein in *Neospora caninum* further accentuates the attenuation of the virulence of the parasite.

In a particular embodiment, the invention relates to a mutant strain of *Neospora* spp in which the function of the NMIC3 protein and the function of the NMIC1 protein are suppressed.

In a particular embodiment, the invention relates to a mutant strain of *Neospora* spp in which both the function of the NMIC3 protein and the function of the NMIC1 protein are suppressed by the inhibition of expression of the two nmic3 and nmic1 genes.

The function of the NMIC3 protein of the mutant strain of *Neospora* spp may be suppressed by:
  a mutation, a deletion or an insertion of one or more nucleotides in the nucleotide sequence of the nmic3 gene or in a nucleotide sequence that determines the expression of the NMIC3 protein, or
  a destabilization of the messenger RNA resulting from the transcription of the nmic3 gene, or
  an inhibition of the translation of the messenger RNA of the nmic3 gene or of a nucleotide sequence that determines the expression of the NMIC3 protein.

The function of the NMIC1 protein of the mutant strain of *Neospora* spp may be suppressed by:
  a mutation, a deletion or an insertion of one or more nucleotides in the nucleotide sequence of the nmic1 gene or in a nucleotide sequence that determines the expression of the NMIC1 protein, or
  a destabilization of the messenger RNA resulting from the transcription of the nmic1 gene, or
  an inhibition of the translation of the messenger RNA of the nmic1 gene or of a nucleotide sequence that determines the expression of the NMIC1 protein.

By "mutation of one or more nucleotides" is meant the substitution, the permutation or the replacement of one or more nucleotides of a nucleotide sequence with one or more nucleotides not present in the wild-type sequence. By "wild-type sequence" is meant the nucleotide sequence found in the natural state in the wild-type strain of the parasite. The wild-type sequence is by definition devoid of all human intervention by genetic engineering. In the present invention, the reference wild-type strain of *N. caninum* is the strain NC1.

By "deletion of one or more nucleotides" is meant the suppression of one or more nucleotides of a nucleotide sequence.

By "insertion of one or more nucleotides" is meant the addition or the integration of one or more nucleotides into a nucleotide sequence.

The mutation, the deletion or the insertion of one or more nucleotides may take place within one or more exons of the corresponding gene and may consequently modify the coding region of said gene, or else may take place within one or more introns and may modify the splice site of a relevant intron. This modification of the splicing site consequently changes the reading frame of the mRNA and leads to the translation of a new protein the amino acid sequence of which differs from the sequence of the so-called wild-type protein.

By "destabilization of the messenger RNA" is meant a decrease in its half-life, i.e. the period of time during which a messenger RNA is available to allow its translation into a protein. The stabilization of messenger RNAs is provided by cis elements (the 5' and 3' UTR sequences flanking the coding sequences of a gene) and trans elements, in proteins capable of binding to the cis elements. The half-life of a messenger RNA may vary in response to various stimuli such as environmental factors, growth factors or hormones. A modification, carried out in vitro by genetic engineering, of the nucleotide sequences of the cis elements is capable of modifying the half-life of the messenger RNA.

By "inhibition of the translation of the messenger RNA of a gene" is meant blocking the translation of the messenger RNA into the protein corresponding to it. In this case, the messenger RNA of a gene is present in the cell, whereas the protein corresponding to it is absent. The inhibition of translation of the messenger RNA of a gene may result from dysfunction of an element of the translation machinery, in particular of the ribosomes, of the ribosomal RNAs (rRNA) or of the transfer RNAs (tRNA), or of the aminoacyl-tRNA synthetases.

In a particular embodiment, the invention relates to a mutant strain of *Neospora* spp, in which:
  the function of the NMIC3 protein is suppressed by a mutation, a deletion or an insertion of one or more nucleotides in the nucleotide sequence of the nmic3 gene, or
  the function of the NMIC1 protein is suppressed by a mutation, a deletion or an insertion of one or more nucleotides in the nucleotide sequence of the nmic1 gene.

In a more particular embodiment, the invention relates to a mutant strain of *Neospora* spp, in which:
  the function of the NMIC3 protein is suppressed by a mutation, a deletion or an insertion of one or more nucleotides in the nucleotide sequence of the nmic3 gene, and optionally
  the function of the NMIC1 protein is suppressed by a mutation, a deletion or an insertion of one or more nucleotides in the nucleotide sequence of the nmic1 gene.

Such a mutation, deletion or insertion of one or more nucleotides in the nucleotide sequence of the nmic3 gene or of the nmic1 gene may lead to the absence of the expression of the NMIC3 or NMIC1 protein, or to the production of a non-functional protein, which may or may not have a certain amino acid sequence identity with that of the NMIC3 or NMIC1 protein.

More particularly, the invention relates to a mutant strain of *Neospora* spp, in which both the function of the NMIC3 protein and the function of the NMIC1 protein are suppressed by a mutation, a deletion or an insertion of one or more nucleotides in the nucleotide sequences of the nmic3 and nmic1 genes.

In another particular embodiment, the invention relates to a mutant strain of *Neospora* spp, in which:
  the function of the NMIC3 protein is suppressed by the deletion of a part or the whole of the nmic3 gene or of its promoter region, or
  the function of the NMIC1 protein is suppressed by the deletion of a part or the whole of the nmic1 gene or of its promoter region.

In another more particular embodiment, the invention relates to a mutant strain of *Neospora* spp, in which:
  the function of the NMIC3 protein is suppressed by the deletion of a part or the whole of the nmic3 gene or of its promoter region, and optionally the function of the NMIC1 protein is suppressed by the deletion of a part or the whole of the nmic1 gene or of its promoter region.

By "deletion of the gene" is meant the suppression of the whole gene, i.e. the introns and the exons, or the entire coding region of the gene, i.e. only the exons. By "promoter region" is meant the nucleotide sequence situated upstream of the transcribed but untranslated 5' UTR region, which serves as a box for the regulation of the expression of a gene.

More particularly, the invention relates to a mutant strain of *Neospora* spp, in which the function of the NMIC3 protein is suppressed by the deletion of a part or the whole of the nmic3 gene or of its promoter region and the function of the NMIC1 protein is suppressed by the deletion of a part or the whole of the nmic1 gene or of its promoter region.

In another particular embodiment, the invention relates to a mutant strain of *Neospora* spp, in which:
the function of the NMIC3 protein is suppressed by a mutation, a deletion or an insertion of one or more nucleotides in a nucleotide sequence that determines the expression of the NMIC3 protein, or
the function of the NMIC1 protein is suppressed by a mutation, a deletion or an insertion of one or more nucleotides in a nucleotide sequence that determines the expression of the NMIC1 protein.

In another more particular embodiment, the invention relates to a mutant strain of *Neospora* spp, in which:
the function of the NMIC3 protein is suppressed by a mutation, a deletion or an insertion of one or more nucleotides in a nucleotide sequence that determines the expression of the NMIC3 protein, and optionally
the function of the NMIC1 protein is suppressed by a mutation, a deletion or an insertion of one or more nucleotides in a nucleotide sequence that determines the expression of the NMIC1 protein.

More particularly, the invention relates to a mutant strain of *Neospora* spp, in which
the function of the NMIC3 protein is suppressed by a mutation, a deletion or an insertion of one or more nucleotides in a nucleotide sequence that determines the expression of the NMIC3 protein, and
the function of the NMIC1 protein is suppressed by a mutation, a deletion or an insertion of one or more nucleotides in a nucleotide sequence that determines the expression of the NMIC1 protein.

In a particular embodiment, the mutant strain of *Neospora* spp according to the present invention is a mutant strain of *Neospora caninum*.

The present invention also has the objective of providing a pharmaceutical composition comprising a mutant strain of *Neospora* in which the function of the NMIC3 protein, and/or the function of the NMIC1 protein, are suppressed.

The present invention also has the objective of providing a pharmaceutical composition comprising a mutant strain of *Neospora* in which the function of the NMIC3 protein, and optionally the function of the NMIC1 protein, are suppressed.

Said pharmaceutical composition comprising a mutant strain as described above and a pharmaceutically acceptable vehicle.

More particularly, a pharmaceutical composition of this kind is administered in a unit dose varying from $10^2$ to $10^9$ tachyzoites of a mutant strain of *Neospora* spp.

More particularly, a pharmaceutical composition of this kind is administered in a unit dose varying from $10^2$ to $10^9$ tachyzoites of the strain Neo nmic1-3 KO.

Even more particularly, such a pharmaceutical composition is administered in a unit dose varying from $10^3$ to $10^8$, in particular from $10^4$ to $10^7$, in particular from $10^5$ to $10^6$ tachyzoites of the strain Neo nmic1-3 KO.

Even more particularly, such a pharmaceutical composition is administered in a unit dose varying from $10^2$ to $10^8$, in particular from $10^2$ to $10^7$, in particular from $10^2$ to $10^6$, in particular from $10^2$ to $10^5$, in particular from $10^2$ to $10^4$, in particular from $10^2$ to $10^3$ tachyzoites of the strain Neo nmic1-3 KO.

Even more particularly, such a pharmaceutical composition is administered in a unit dose of $10^2$, $10^3$, $10^4$, $10^5$, $10^6$, $10^7$, $10^8$, or $10^9$ tachyzoites of the strain Neo nmic1-3 KO.

In a more particular embodiment, the first administration may be followed by possible subsequent boosters, according to the unit doses stated above.

Moreover, the present invention has the objective of supplying a vaccine composition comprising a *Neospora* spp mutant strain according to the present invention and a pharmaceutically acceptable vehicle.

Such a pharmaceutical composition or vaccine composition may be administered by parenteral route (intravenous, subcutaneous, intradermal, intramuscular, and intraperitoneal) or by enteral route.

The choice of an acceptable pharmaceutical vehicle contained in such a pharmaceutical composition or vaccine composition may be made in relation to the method of administration envisaged, based on the knowledge of a person skilled in the art.

Such a pharmaceutical or vaccine composition may be used for the treatment of neosporosis of primary infection, of reactivation or of reinfection in pet animals, such as dogs and horses, and farm animals, such as ovines, caprins, bovines, porcines, camelids and cervids.

More particularly, such a pharmaceutical or vaccine composition may be used for the treatment of neosporosis of primary infection, of reactivation or of reinfection in companion animals, such as dogs and horses, and farm animals, such as ovines, caprins, bovines, porcines, camelids and cervids and in particular for preventing the maternal-foetal transmission of the parasite in order to reduce the number of abortions but also the risk of vertical contamination from mothers to their offspring.

Even more particularly, such a pharmaceutical or vaccine composition may be used for the treatment of neosporosis of primary infection, of reactivation or of reinfection in pet animals, such as dogs and horses, and farm animals, such as ovines, caprins, bovines, porcines, camelids and cervids and in particular for preventing the maternal-foetal transmission of the parasite in order to reduce the number of abortions but also the risk of vertical contamination from mothers to their offspring in the case of infection during gestation (i.e. acute infection) but also prior to gestation (i.e. chronic infection).

The invention also relates to a method of in vitro diagnostics for differentiating the animals vaccinated with the mutant strains Neo ncmic1 KO, Neo ncmic3 KO, Neo ncmic1-3 KO and animals naturally infected by the wild-type strains of *N. caninum*. These diagnostic tests, called DIVA (Differentiating infected from Vaccinated Animal), are being required more and more by the regulatory authorities in particular for purposes of pharmacovigilance and epidemiological studies but also in order to identify the possible causes of abortions occurring in the vaccinated animals.

The present invention also relates to a method of in vitro differential diagnostics for discriminating a mammal vaccinated with the compositions of the invention from an unvaccinated mammal, said method comprising a step of:

determination of the concentration of anti-NMIC1 and/or anti-NMIC3 and/or anti-DHFR and/or anti-CAT-GFP antibodies, and/or, determination of the concentration of NMIC1 and/or NMIC3 and/or DHFR and/or CAT-GFP antigen, determination of the expression level of the nmic1, nmic3, dhfr and/or cat-gfp genes, and/or determination of the presence or absence of the nmic1, nmic3, dhfr and/or cat-gfp genes, in a biological sample from the aforesaid mammal.

The present invention also relates to a method of in vitro differential diagnostics for discriminating a mammal vaccinated with the compositions of the invention from an unvaccinated mammal, said method comprising the following steps:

i) determination of the concentration of anti-NMIC1 and/or anti-NMIC3 and/or anti-DHFR and/or anti-CAT-GFP antibodies, and/or, determination of the concentration of NMIC1 and/or NMIC3 and/or DHFR and/or CAT-GFP antigen, ii) determination of the expression level of the genes nmic1, nmic3, dhfr and/or catand/or, determination of the presence or absence of the nmic1, nmic3, dhfr and/or cat-gfp genes, in a biological sample from the aforesaid mammal.

According to a particular embodiment, the method of the invention may be implemented on a biological sample selected from the group constituted by blood and serum but also certain tissues and organs such as the placenta, the brain, the muscles, etc.

The wild-type strains of *Neospora caninum* have the ncmic1 and ncmic3 genes in their genome and express the NcMIC1 and NcMIC3 proteins.

The mutant strains of *Neospora caninum* as defined according to the present invention have, respectively:

the ncmic1 gene and the dhfr selection gene for the mutant strain Neo ncmic3 KO; the dhfr selection gene is inserted by homologous recombination in place of the ncmic3 gene into the genome of this mutant strain. The mutant strain Neo ncmic3 KO expresses the NcMIC1 and DHFR proteins and does not express the NcMIC3 protein, the ncmic3 gene and the cat-gfp selection gene for the mutant strain Neo ncmic1 KO; the cat-gfp selection gene is inserted by homologous recombination in place of the ncmic1 gene into the genome of this mutant strain. The mutant strain Neo ncmic1 KO expresses the NcMIC3 and CAT-GFP proteins and does not express the NcMIC1 protein, the dhfr and cat-gfp selection genes for the mutant strain Neo ncmic1-3 KO; the dhfr and cat-gfp selection genes are inserted by homologous recombination in place of the ncmic3 and ncmic1 gene respectively into the genome of this mutant strain. The mutant strain Neo ncmic1-3 KO expresses the DHFR and CAT-GFP proteins and does not express the NcMIC1 and NcMIC3 proteins.

Diagnostics between animals vaccinated with the mutant strains of the invention and animals infected by wild-type strains of *N. caninum* may be indirect, based on the detection and the identification of antibodies, or direct, based on the detection of the infectious agent with immunology or molecular technologies.

The present invention also relates to a method for the detection, in a biological sample in particular selected from the group constituted by blood and serum obtained from a mammal, of an anti-NMIC1 antibody and/or an anti-NMIC3 antibody and/or an anti-DHFR antibody and/or an anti-CAT-GFP antibody, said method comprising the following step:

determination of the presence of at least one antibody present in a biological sample previously taken from a mammal by the in vitro formation of an immune complex, said immune complex being constituted by the NMIC1 protein bound to the anti-NMIC1 antibody or the NMIC3 protein bound to the anti-NMIC3 antibody or the DHFR protein bound to the anti-DHFR antibody or the CAT-GFP protein bound to the anti-CAT-GFP antibody, by comparison with a reference biological sample.

By "immune complex" is meant the physical interaction between an antigen and an antibody specifically directed against this antigen. In the present invention, this interaction takes place in vitro between the NMIC1, NMIC3, DHFR, CAT-GFP proteins and the antibodies specifically directed against each of these proteins.

By "detection and identification of antibodies" is meant the detection of specific antibodies of the sought antigens present in the serum of the individuals. The detection of the antibodies is carried out by conventional indirect ELISA or competitive ELISA techniques.

The indirect ELISA techniques are based on the use of antigens fixed on solid supports. The serum from the individuals to be diagnosed is deposited on the support in order to generate interactions between the fixed antigen and any antibodies present in the serum of the individuals to be diagnosed. After washing, the antigen-antibody interaction is detected using labelled secondary antibodies specifically recognizing the conjugated anti-species antibodies. The detection of antibodies directed against the DHFR and/or CAT-GFP proteins will demonstrate previous inoculation of the individual with the mutant strains. Conversely, the detection of antibodies directed against the NcMIC1 and NcMIC3 proteins will demonstrate previous contamination of the individual with a wild-type strain of *N. caninum.*

Competitive ELISA is based on the competition between the antibodies optionally present in the serum of the individual to be diagnosed and the antibodies present in a detection serum. The antigens are fixed on solid supports. The serum of the individuals to be diagnosed and the competitive serum are deposited on the support. The specific binding of the detection antibody is detected using an appropriate and labelled anti-species conjugate. The possible presence of antibodies in the serum of the individual to be diagnosed generates competition with the antibodies present in the detection serum and leads to a decrease in detection. Indirect ELISA with the DHFR and/or CAT-GFP proteins will make it possible to detect the inoculation of the animal with the mutant strains of the invention. Indirect ELISA with the NcMIC1 and NcMIC3 proteins will make it possible to detect the contamination of the animal with a wild-type strain of *N. caninum.*

The present invention also relates to a method for the detection, in a biological sample in particular selected from the group constituted by blood and serum but also certain tissues and organs such as the placenta, the brain, the muscles, etc. obtained from a mammal, of the NMIC1 antigen and/or the NMIC3 antigen and/or the DHFR antigen and/or the CAT-GFP antigen, said method comprising the following step:

determination of the presence of at least one antigen in a biological sample previously taken from a mammal by the in vitro formation of an immune complex, said immune complex being constituted by the NMIC1 protein bound to the anti-NMIC1 antibody or the NMIC3 protein bound to the anti-NMIC3 antibody or the DHFR protein bound to the anti-DHFR antibody or the CAT-GFP protein bound to the anti-CAT-GFP antibody, by comparison with a reference biological sample.

In a more particular embodiment, the present invention relates to a method for the detection of the NMIC1 and/or NMIC3 and/or DHFR and/or CAT-GFP antigens and the anti-NMIC1 and/or anti-NMIC3 and/or anti-DHFR and/or anti-CAT-GFP antibodies. By "detection of the infectious agent with immunology technologies" is meant all of the techniques allowing the detection of specific antigenic proteins of the wild-type strains of N. caninum (i.e. NcMIC1 and NcMIC3 proteins) and specific proteins of the mutant strains of the invention (i.e. DHFR and/or CAT-GFP proteins).

The detection of the antigenic proteins may result from experiments of immunohistochemistry, immune transfer, an immuno-enzymatic method with antigen capture (ELISA, enzyme-linked immunosorbent assay), immunochromatography or proteomics that are well known to a person skilled in the art. These assays may be carried out with various biological samples.

By "immunohistochemistry" is meant the detection of antigens in fixed tissues using labelled antibodies directed specifically against the antigen. Immunohistochemistry with specific antibodies of the DHFR and/or CAT-GFP proteins will make it possible to detect the inoculation of the animal with the mutant strains of the invention. Immunohistochemistry with specific antibodies of the NcMIC1 and NcMIC3 proteins will make it possible to detect the contamination of the animal with a wild-type strain of N. caninum.

By "immune transfer" is meant the detection of antigens in biological samples after separation of the proteins of the sample by gel electrophoresis and detection with labelled antibodies directed specifically against the antigen. Immune transfer with specific antibodies of the DHFR and/or CAT-GFP proteins will make it possible to detect the inoculation of the animal with the mutant strains. Immune transfer with specific antibodies of the NMIC1 and NMIC3 proteins will make it possible to detect the contamination of the animal with a wild-type strain.

By "enzyme-linked immunosorbent assay (ELISA)" is meant the detection of antigens using capture antibodies directed specifically against the antigen and fixed on a solid plate (indirect ELISA of the sandwich type). The antigen present in the sample is captured by the specific antibody and then its presence is revealed by a second labelled antibody. ELISA with specific antibodies of the DHFR and/or CAT-GFP proteins will make it possible to detect the inoculation of the animal with the mutant strains of the invention. ELISA with specific antibodies of the NcMIC1 and NcMIC3 proteins will make it possible to detect the contamination of the animal with a wild-type strain of N. caninum.

By "immunochromatography" is meant a method for the detection of antigens based on the purification of the sample by affinity chromatography using a specific antibody of the antigen labelled and fixed on a chromatography column. Immunochromatography with specific antibodies of the DHFR and/or CAT-GFP proteins will make it possible to detect the inoculation of the animal with the mutant strains of the invention. Immunochromatography with specific antibodies of the NcMIC1 and NcMIC3 proteins will make it possible to detect the contamination of the animal with a wild-type strain of N. caninum.

By "detection of the infectious agent with molecular technologies" is meant the techniques of molecular biology that are well known to a person skilled in the art for the identification of the presence of specific nucleotide sequences of the wild-type strains and the mutant strains and in particular by the amplification by the polymerase chain reaction (PCR), real-time PCR, by diagnostics by restriction fragment length polymorphism (RFLP), which may be linked to PCR methods or by diagnostics using nucleic acid probes.

In a particular embodiment, the invention relates to an oligonucleotide consisting of a nucleic acid sequence selected from the group comprising SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49 or their complementary sequences.

| Name of the primer | Sequence 5'→3' | No. of sequence |
|---|---|---|
| ATG Ncmic1 | ATGGGCCAGTCGGTGGTTTT | SEQ ID NO: 35 |
| ATG Ncmic3 | ATGCGTGGCGGGGCGTCCGC | SEQ ID NO: 36 |
| ATG DHFR | ATGCAGAAACCGGTGTGTC | SEQ ID NO: 37 |
| ATG CATGFP | ATGCATGAGAAAAAAATCACTG | SEQ ID NO: 38 |
| stop Ncmic1 | TTACAATTCAGATTCACCCG | SEQ ID NO: 39 |
| stop Ncmic3 | TTATCGAGCCGTTCCGCATTTG | SEQ ID NO: 40 |
| stop DHFR | CTAGACAGCCATCTCCATCTG | SEQ ID NO: 41 |
| stop CATGFP | TTAATCGAGCGGGTCCTGGT | SEQ ID NO: 42 |
| Olig 1 | CAGATGGAGATGGCTGTCTAG | SEQ ID NO: 43 |
| Olig 2 | CGCTTTCGTTCTGATTGACA | SEQ ID NO: 44 |
| Olig 3 | AAAACCACCGACTGGCCCAT | SEQ ID NO: 45 |
| Olig 4 | TCCTCTCGTTGTTGGAAGCT | SEQ ID NO: 46 |
| Olig 5 | TAGCACGGGAAAGGATTGAC | SEQ ID NO: 47 |
| Olig 6 | CAAGATCCGCCACAACATC | SEQ ID NO: 48 |
| ORF CATGFP F3 | TTCATCATGCCGTTTGTGAT | SEQ ID NO: 49 |

By "oligonucleotide" is meant a nucleic acid sequence that can be used as a primer in an amplification method or as a probe in a detection method. In the present invention, the oligonucleotides consist of a sequence of at least 15, preferably 20 nucleotides, and preferably less than 30 nucleotides, capable of hybridizing to a molecule of genomic DNA or to a complementary DNA. By "hybridization" is meant the physical interaction occurring between two nucleic acid molecules. This hybridization may involve DNA/DNA or RNA/RNA homoduplexes or DNA/RNA heteroduplexes.

By "nucleic acid" is meant a succession of nucleotides joined together by phosphodiester bonds. A nucleic acid molecule may be linear, circular, single-stranded, double-stranded, or partially double-stranded. The nucleic acid sequences are described in the present invention according to the usage that is well known to a person skilled in the art, i.e. they are defined by a sequence numbered in the 5' to 3' direction.

By "complementary sequences" is meant two nucleic acid sequences that have complementary nucleotides that may interact with one another via hydrogen bonds. Opposite to an adenine, there is always a thymine or a uracil (in the case of a DNA/RNA heteroduplex); opposite to a cytosine, there is always a guanine. By way of example, without limiting the scope of the invention, the sequence 5' ATCG 3' and the sequence 5' CGAT 3' are complementary.

The invention also relates to the pairs of oligonucleotides consisting of the pairs of sequences selected from:
  SEQ ID NO: 21 and SEQ ID NO: 25, SEQ ID NO: 21 and SEQ ID NO: 28, SEQ ID NO: 21 and SEQ ID NO: 35, SEQ ID NO: 21 and SEQ ID NO: 46,
  SEQ ID NO: 39 and SEQ ID NO: 25, SEQ ID NO: 39 and SEQ ID NO: 28, SEQ ID NO: 39 and SEQ ID NO: 35, SEQ ID NO: 39 and SEQ ID NO: 46, SEQ ID NO: 39 and SEQ ID NO: 24,
  SEQ ID NO: 27 and SEQ ID NO: 28, SEQ ID NO: 27 and SEQ ID NO: 35, SEQ ID NO: 27 and SEQ ID NO: 46, SEQ ID NO: 27 and SEQ ID NO: 24,
  SEQ ID NO: 45 and SEQ ID NO: 46, SEQ ID NO: 45 and SEQ ID NO: 24,
  SEQ ID NO: 47 and SEQ ID NO: 46, SEQ ID NO: 47 and SEQ ID NO: 24,
  SEQ ID NO: 26 and SEQ ID NO: 24,
  SEQ ID NO: 11 and SEQ ID NO: 12, SEQ ID NO: 11 and SEQ ID NO: 8, SEQ ID NO: 11 and SEQ ID NO: 40, SEQ ID NO: 11 and SEQ ID NO: 6,
  SEQ ID NO: 5 and SEQ ID NO: 12, SEQ ID NO: 5 and SEQ ID NO: 8, SEQ ID NO: 5 and SEQ ID NO: 40, SEQ ID NO: 5 and SEQ ID NO: 6, SEQ ID NO: 5 and SEQ ID NO: 14,
  SEQ ID NO: 7 and SEQ ID NO: 12, SEQ ID NO: 7 and SEQ ID NO: 8, SEQ ID NO: 7 and SEQ ID NO: 40, SEQ ID NO: 7 and SEQ ID NO: 6, SEQ ID NO: 7 and SEQ ID NO: 14,
  SEQ ID NO: 36 and SEQ ID NO: 8, SEQ ID NO: 36 and SEQ ID NO: 40, SEQ ID NO: 36 and SEQ ID NO: 6, SEQ ID NO: 36 and SEQ ID NO: 14, SEQ ID NO: 36 and SEQ ID NO: 12,
  SEQ ID NO: 15 and SEQ ID NO: 6, SEQ ID NO: 15 and SEQ ID NO: 14,
  SEQ ID NO: 11 and SEQ ID NO: 13, SEQ ID NO: 11 and SEQ ID NO: 10, SEQ ID NO: 11 and SEQ ID NO: 41, SEQ ID NO: 11 and SEQ ID NO: 44, SEQ ID NO: 11 and SEQ ID NO: 6,
  SEQ ID NO: 5 and SEQ ID NO: 13, SEQ ID NO: 5 and SEQ ID NO: 10, SEQ ID NO: 5 and SEQ ID NO: 41, SEQ ID NO: 5 and SEQ ID NO: 44, SEQ ID NO: 5 and SEQ ID NO: 6, SEQ ID NO: 5 and SEQ ID NO: 14,
  SEQ ID NO: 37 and SEQ ID NO: 10, SEQ ID NO: 37 and SEQ ID NO: 41, SEQ ID NO: 37 and SEQ ID NO: 44, SEQ ID NO: 37 and SEQ ID NO: 6, SEQ ID NO: 37 and SEQ ID NO: 14,
  SEQ ID NO: 9 and SEQ ID NO: 10, SEQ ID NO: 9 and SEQ ID NO: 41, SEQ ID NO: 9 and SEQ ID NO: 44, SEQ ID NO: 9 and SEQ ID NO: 6, SEQ ID NO: 9 and SEQ ID NO: 14,
  SEQ ID NO: 43 and SEQ ID NO: 44, SEQ ID NO: 43 and SEQ ID NO: 6, SEQ ID NO: 43 and SEQ ID NO: 14,
  SEQ ID NO: 16 and SEQ ID NO: 44, SEQ ID NO: 16 and SEQ ID NO: 6, SEQ ID NO: 16 and SEQ ID NO: 14,
  SEQ ID NO: 21 and SEQ ID NO: 22, SEQ ID NO: 21 and SEQ ID NO: 30, SEQ ID NO: 21 and SEQ ID NO: 42,
  SEQ ID NO: 38 and SEQ ID NO: 30, SEQ ID NO: 38 and SEQ ID NO: 42, SEQ ID NO: 38 and SEQ ID NO: 24,
  SEQ ID NO: 49 and SEQ ID NO: 30, SEQ ID NO: 49 and SEQ ID NO: 42, SEQ ID NO: 49 and SEQ ID NO: 24,
  SEQ ID NO: 29 and SEQ ID NO: 30, SEQ ID NO: 29 and SEQ ID NO: 42, SEQ ID NO: 29 and SEQ ID NO: 24,
  SEQ ID NO: 23 and SEQ ID NO: 30, SEQ ID NO: 23 and SEQ ID NO: 42, SEQ ID NO: 23 and SEQ ID NO: 24,
  SEQ ID NO: 48 and SEQ ID NO: 30, SEQ ID NO: 48 and SEQ ID NO: 42, SEQ ID NO: 48 and SEQ ID NO: 24,
  or their complementary sequences.

By "pair of oligonucleotides" is meant two nucleotides as defined by their sequences.

Another purpose of the invention is to offer sets of oligonucleotides consisting of the triads of sequences selected from:
  SEQ ID NO: 7 and SEQ ID NO: 12 and SEQ ID NO: 36,
  SEQ ID NO: 43 and SEQ ID NO: 44 and SEQ ID NO: 16,
  SEQ ID NO: 45 and SEQ ID NO: 46 and SEQ ID NO: 47,
  SEQ ID NO: 23 and SEQ ID NO: 30 and SEQ ID NO: 48,
  or their complementary sequences.

For each triad, the first two SEQ IDs correspond to the primers and the third corresponds to the sequence of the probe.

By "sets of oligonucleotides" is meant groups of three oligonucleotides as defined by their respective sequences.

The wild-type strains of *Neospora caninum* have the ncmic1 and ncmic3 genes in their genome.

Analysis of a biological sample for the presence and/or the expression level of the four ncmic1, ncmic3, dhfr, cat-gfp genes makes it possible to determine whether the animal is a carrier of a strain of *Neospora caninum* resulting from an infection by a wild-type strain or resulting from a vaccination with one of the three mutant strains as described in the present invention. The purpose is to be able to establish a differential diagnosis that makes it possible to discriminate the vaccinated animals from the unvaccinated and/or infected animals, within a herd.

The invention also relates to the use of at least one oligonucleotide consisting of a nucleic acid sequence selected from the group comprising SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49 or their complementary sequences, for the detection of ncmic1, and/or ncmic3, and/or dhfr, and/or cat-gfp genes derived from the genome of wild-type strains and/or of the mutant strains Neo ncmic1 KO and/or Neo ncmic3 KO and/or Neo ncmic1-3 KO of *Neospora caninum*.

In a particular embodiment, the invention relates to the use of at least one oligonucleotide consisting of the sequence selected from SEQ ID NO: 21, SEQ ID NO: 24, SEQ ID NO: 25, SEQ ID NO: 26, SEQ ID NO: 27, SEQ ID NO: 28, SEQ ID NO: 35, SEQ ID NO: 39, SEQ ID NO: 45, SEQ ID NO: 46, SEQ ID NO: 47 or their complementary sequence, as a primer for carrying out a hybridization and optionally an amplification of the ncmic1 gene originating from the genome of wild-type strains and/or of the mutant strain Neo ncmic3 KO of *Neospora caninum*.

In a more particular embodiment, the invention relates to the use of oligonucleotides consisting of at least one pair of sequences selected from: SEQ ID NO: 21 and SEQ ID NO: 25, SEQ ID NO: 21 and SEQ ID NO: 28, SEQ ID NO: 21 and SEQ ID NO: 35, SEQ ID NO: 21 and SEQ ID NO: 46, SEQ ID NO: 39 and SEQ ID NO: 25, SEQ ID NO: 39 and SEQ ID NO: 28, SEQ ID NO: 39 and SEQ ID NO: 35, SEQ ID NO: 39 and SEQ ID NO: 46, SEQ ID NO: 39 and SEQ ID NO: 24, SEQ ID NO: 27 and SEQ ID NO: 28, SEQ ID NO: 27 and SEQ ID NO: 35, SEQ ID NO: 27 and SEQ ID NO: 46, SEQ ID NO: 27 and SEQ ID NO: 24, SEQ ID NO: 45 and SEQ ID NO: 46, SEQ ID NO: 45 and SEQ ID NO: 24, SEQ ID NO: 47 and SEQ ID NO: 46, SEQ ID NO: 47 and SEQ ID NO: 24, SEQ ID NO: 26 and SEQ ID NO: 24, or their complementary sequences, as primers for carrying out a hybridization and optionally an amplification of the ncmic1 gene originating from the genome of wild-type strains and/or of the mutant strain Neo ncmic3 KO of *Neospora caninum.*

In another particular embodiment, the invention relates to the use of at least one oligonucleotide consisting of the sequence selected from SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 36, SEQ ID NO: 40, or their complementary sequence, as a primer for carrying out a hybridization and optionally an amplification of the ncmic3 gene originating from the genome of wild-type strains and/or of the mutant strain Neo ncmic1 KO of *Neospora caninum.*

In another more particular embodiment, the invention relates to the use of oligonucleotides consisting of at least one pair of sequences selected from SEQ ID NO: 11 and SEQ ID NO: 12, SEQ ID NO: 11 and SEQ ID NO: 8, SEQ ID NO: 11 and SEQ ID NO: 40, SEQ ID NO: 11 and SEQ ID NO: 6, SEQ ID NO: 5 and SEQ ID NO: 12, SEQ ID NO: 5 and SEQ ID NO: 8, SEQ ID NO: 5 and SEQ ID NO: 40, SEQ ID NO: 5 and SEQ ID NO: 6, SEQ ID NO: 5 and SEQ ID NO: 14, SEQ ID NO: 7 and SEQ ID NO: 12, SEQ ID NO: 7 and SEQ ID NO: 8, SEQ ID NO: 7 and SEQ ID NO: 40, SEQ ID NO: 7 and SEQ ID NO: 6, SEQ ID NO: 7 and SEQ ID NO: 14, SEQ ID NO: 36 and SEQ ID NO: 8, SEQ ID NO: 36 and SEQ ID NO: 40, SEQ ID NO: 36 and SEQ ID NO: 6, SEQ ID NO: 36 and SEQ ID NO: 14, SEQ ID NO: 36 and SEQ ID NO: 12, SEQ ID NO: 15 and SEQ ID NO: 6, SEQ ID NO: 15 and SEQ ID NO: 14, or their complementary sequences, as primers for carrying out a hybridization and optionally an amplification of the ncmic3 gene originating from the genome of wild-type strains and/or of the mutant strain Neo ncmic1 KO of *Neospora caninum.*

In yet another particular embodiment, the invention relates to the use of at least one oligonucleotide consisting of the sequence selected from SEQ ID NO: 5, SEQ ID NO: 6, SEQ ID NO: 9, SEQ ID NO: 10, SEQ ID NO: 11, SEQ ID NO: 13, SEQ ID NO: 14, SEQ ID NO: 16, SEQ ID NO: 37, SEQ ID NO: 41, SEQ ID NO: 43, SEQ ID NO: 44, or their complementary sequence, as a primer for carrying out a hybridization and optionally an amplification of the dhfr selection gene originating from the genome of the mutant strains Neo ncmic3 KO and/or Neo ncmic1-3 KO of *Neospora caninum.*

In yet another more particular embodiment, the invention relates to the use of oligonucleotides consisting of at least one pair of sequences selected from: SEQ ID NO: 11 and SEQ ID NO: 13, SEQ ID NO: 11 and SEQ ID NO: 10, SEQ ID NO: 11 and SEQ ID NO: 41, SEQ ID NO: 11 and SEQ ID NO: 44, SEQ ID NO: 11 and SEQ ID NO: 6, SEQ ID NO: 5 and SEQ ID NO: 13, SEQ ID NO: 5 and SEQ ID NO: 10, SEQ ID NO: 5 and SEQ ID NO: 41, SEQ ID NO: 5 and SEQ ID NO: 44, SEQ ID NO: 5 and SEQ ID NO: 6, SEQ ID NO: 5 and SEQ ID NO: 14, SEQ ID NO: 37 and SEQ ID NO: 10, SEQ ID NO: 37 and SEQ ID NO: 41, SEQ ID NO: 37 and SEQ ID NO: 44, SEQ ID NO: 37 and SEQ ID NO: 6, SEQ ID NO: 37 and SEQ ID NO: 14, SEQ ID NO: 9 and SEQ ID NO: 10, SEQ ID NO: 9 and SEQ ID NO: 41, SEQ ID NO: 9 and SEQ ID NO: 44, SEQ ID NO: 9 and SEQ ID NO: 6, SEQ ID NO: 9 and SEQ ID NO: 14, SEQ ID NO: 43 and SEQ ID NO: 44, SEQ ID NO: 43 and SEQ ID NO: 6, SEQ ID NO: 43 and SEQ ID NO: 14, SEQ ID NO: 16 and SEQ ID NO: 44, SEQ ID NO: 16 and SEQ ID NO: 6, SEQ ID NO: 16 and SEQ ID NO: 14, or their complementary sequences, as primers for carrying out a hybridization and optionally an amplification of the dhfr selection gene originating from the genome of mutant strains Neo ncmic3 KO and/or Neo ncmic1-3 KO of *Neospora caninum.*

In yet another particular embodiment, the invention relates to the use of at least one oligonucleotide consisting of the sequence selected from SEQ ID NO: 21, SEQ ID NO: 22, SEQ ID NO: 23, SEQ ID NO: 24, SEQ ID NO: 29, SEQ ID NO: 30, SEQ ID NO: 38, SEQ ID NO: 42, SEQ ID NO: 48, SEQ ID NO: 49 or their complementary sequence, as a primer for carrying out a hybridization and optionally an amplification of the cat-gfp selection gene originating from the genome of the mutant strains Neo ncmic1 KO and/or Neo ncmic1-3 KO of *Neospora caninum.*

In yet another more particular embodiment, the invention relates to the use of oligonucleotides consisting of at least one pair of sequences selected from: SEQ ID NO: 21 and SEQ ID NO: 22, SEQ ID NO: 21 and SEQ ID NO: 30, SEQ ID NO: 21 and SEQ ID NO: 42, SEQ ID NO: 38 and SEQ ID NO: 30, SEQ ID NO: 38 and SEQ ID NO: 42, SEQ ID NO: 38 and SEQ ID NO: 24, SEQ ID NO: 49 and SEQ ID NO: 30, SEQ ID NO: 49 and SEQ ID NO: 42, SEQ ID NO: 49 and SEQ ID NO: 24, SEQ ID NO: 29 and SEQ ID NO: 30, SEQ ID NO: 29 and SEQ ID NO: 42, SEQ ID NO: 29 and SEQ ID NO: 24, SEQ ID NO: 23 and SEQ ID NO: 30, SEQ ID NO: 23 and SEQ ID NO: 42, SEQ ID NO: 23 and SEQ ID NO: 24, SEQ ID NO: 48 and SEQ ID NO: 30, SEQ ID NO: 48 and SEQ ID NO: 42, SEQ ID NO: 48 and SEQ ID NO: 24, or their complementary sequences, as primers for carrying out a hybridization and optionally an amplification of the cat-gfp selection gene originating from the genome of mutant strains Neo ncmic1 KO and/or Neo ncmic1-3 KO of *Neospora caninum.*

By "amplification" is meant the increase in the concentration of a specific DNA sequence among a mixture of DNA sequences. The techniques of DNA amplification are techniques that are well known to a person skilled in the art.

The invention also relates to the use of at least one oligonucleotide consisting of a nucleic acid sequence selected from the group comprising SEQ ID NO: 35 to 42, SEQ ID NO: 16, SEQ ID NO: 47, SEQ ID NO: 48, or of its complementary sequence, as a probe for carrying out a hybridization with a nucleic acid originating from the genome of wild-type strains and/or of the mutant strains Neo ncmic1 KO and/or Neo ncmic3 KO and/or Neo ncmic1-3 KO of *Neospora caninum.*

The invention also relates to the use of the oligonucleotide consisting of a nucleic acid sequence selected from the group comprising SEQ ID NO: 35 to 42, SEQ ID NO: 16, SEQ ID NO: 47, SEQ ID NO: 48, or of its complementary sequence, the aforesaid oligonucleotide being labelled with a fluorophore at one end and optionally with a quencher at the other end.

By "fluorophore" is meant the molecules capable of emitting light when they are excited by a light source. The fluorophores are molecules that are well known to a person skilled in the art, those most used being Fam, Tet, Hex, Tamra, Texas Red, Cy3, Cy5. The purpose of this non limitative list is to illustrate the fluorophore concept but should in no case restrict the present invention to the use of only these fluorophores.

By "quencher" is meant a chemical species capable of deactivating an excited state created in a molecular entity by energy transfer, by electron transfer or by a chemical mechanism. Quenchers are molecules that are well known to a person skilled in the art, those most used being Dabcyl, Eclipse Dark Quencher, Black Hole Quencher. A fluorophore may also serve as a quencher. For this, the emission spectrum of the fluorophore grafted at 5' must not overlap the excitation spectrum of the fluorophore-quencher grafted at 3'. The purpose of this non limitative list is to illustrate the quencher concept but should in no case restrict the present invention to the use of only these quenchers.

In the present invention, the probes used may come under the definition of Taqman, FRET (Fluorescent Resonance Energy Transfer), Molecular Beacon or Scorpion technology or any other real-time PCR (or RT-PCR) technology that are well known to a person skilled in the art.

The invention also relates to a method for the detection of *Neospora caninum* by in vitro amplification starting from a biological sample, said method comprising the steps of:
   bringing the set of oligonucleotides as defined above into contact with a biological sample, or a nucleic acid originating from the aforesaid biological sample, under conditions allowing the oligonucleotides to hybridize to a nucleic acid of *Neospora caninum* present in the aforesaid sample,
   amplifying the nucleic acid of *Neospora caninum* using the oligonucleotides as primers,
   detectioning the amplification product characterizing the presence of *Neospora caninum* in the sample.

According to a particular embodiment, the detection method according to the invention may be implemented on a biological sample selected from the group consisting of blood, serum or plasma, but also certain tissues and organs such as the placenta, the brain, the muscles, etc.

According to another embodiment, in the method for the detection of *Neospora caninum*, the nucleic acid of *Neospora caninum* is amplified by PCR. The PCR may be qualitative, quantitative or semiquantitative. According to whether or not a detection probe is used, it is called real-time PCR or conventional PCR.

According to another more particular embodiment, in the method for the detection of *Neospora caninum*, the amplification product is detected using at least one of the oligonucleotides of sequence SEQ ID NO: 35 to 42, SEQ ID NO: 16, SEQ ID NO: 47, SEQ ID NO: 48, or its complementary sequence, or any other oligonucleotide with a sequence included in that of the amplicon obtained from the primers allowing the amplification of the gene fragment of interest, labelled with a fluorophore at one end and with a quencher, as probe, at the other end.

The invention also relates to a kit for the amplification of *Neospora caninum* starting from a biological sample, said kit comprising one of the aforesaid sets of oligonucleotides, or their complementary sequences, and means allowing the amplification of a nucleic acid of *Neospora caninum*.

According to a particular embodiment, said amplification kit comprises:
   at least one set of oligonucleotides consisting of the oligonucleotides of sequences
   SEQ ID NO: 7 and SEQ ID NO: 12 and SEQ ID NO: 36,
   SEQ ID NO: 43 and SEQ ID NO: 44 and SEQ ID NO: 16,
   SEQ ID NO: 45 and SEQ ID NO: 46 and SEQ ID NO: 47,
   SEQ ID NO: 23 and SEQ ID NO: 30 and SEQ ID NO: 48,
   and
   means for amplifying a nucleic acid of *Neospora caninum*,
   optionally an internal control.

By "means for amplifying a nucleic acid" is meant the dNTPs, a Taq Polymerase, the salts and buffers for carrying out a PCR.

By "internal control" is meant a nucleic acid sequence (exogenous DNA) unrelated to the genome of *Neospora caninum*, primers and a probe allowing the amplification and the detection of this exogenous DNA. This internal control is placed in the mix used for PCR for the detection of *Neospora caninum* and provides evidence of the correct operation of amplification.

The following figures and examples provide further illustration of the present invention.

FIG. 1: this figure illustrates the 2 steps of homologous recombination for obtaining the strain Neo ncmic1-3 KO. The first step of homologous recombination allows the integration of the gene coding for the enzyme dihydrofolate reductase (DHFR) at the locus of the ncmic3 gene. A selection with pyrimethamine makes it possible to amplify the mutant single strain Neo ncmic3 KO. The strain Neo ncmic3 KO thus obtained is used for the second step of homologous recombination which allows the integration of the gene coding for the chimeric protein chloramphenicol-acetyl-transferase/green fluorescent protein (CAT-GFP) at the locus of the ncmic1 gene. A selection with chloramphenicol then allows amplification of the mutant double strain Neo ncmic1-3 KO.

FIG. 2-A: this figure is a schematic representation of the pNcMic3KO-DHFR plasmid. This plasmid of 11,312 base pairs comprises the dhfr selection gene flanked by the homologous regions (5HR-NcMic3 and 3HR-NcMic3) of the sequences flanking the ncmic3 gene, the ampicillin resistance gene (Amp) as well as the Not I restriction site which permits its linearization.

FIG. 2-B: this figure is a schematic representation of the pNcMic1KO-CAT-GFP plasmid. This plasmid of 10,069 base pairs comprises the cat-gfp selection gene flanked by the homologous regions (3HR-NcMic1 and 5HR-NcMic1) of the sequences flanking the ncmic1 gene, the ampicillin resistance gene (Amp) as well as the Kpn I restriction site which permits its linearization.

FIG. 3-A: this figure shows the electrophoretic profiles of the PCR products obtained respectively in the wild-type strain NC1 of *N. caninum* and in the mutant strain Neo ncmic3 KO, using the sets of PCR primers No. 1, No. 2 or No. 3 in Table II which correspond to SEQ ID NO: 5 to SEQ ID NO: 10.

FIG. 3-B: this figure shows the electrophoretic profiles of the PCR products obtained respectively in the wild-type strain NC1 of *N. caninum* and in the mutant strain Neo ncmic3 KO, using the sets of PCR primers No. 4, No. 5, No. 6 or No. 7 in Table II which correspond to SEQ ID NO: 11 to SEQ ID NO: 16.

FIG. 4-A: this figure illustrates the analysis for detecting the NcMIC3 protein in the wild-type strain NC1 of *N. caninum* by immunofluorescence, using an antibody specifically recognizing the NcMIC3 protein. One and the same microscopic field is visualized in direct light (image A) or in fluorescence (image B).

FIG. 4-B: this figure illustrates the analysis for detecting the NcMIC3 protein in the mutant strain of *N. caninum* Neo ncmic3 KO by immunofluorescence, using an antibody specifically directed against the NcMIC3 protein. One and the same microscopic field is visualized in direct light (image A) or in fluorescence (image B).

Figure 5:
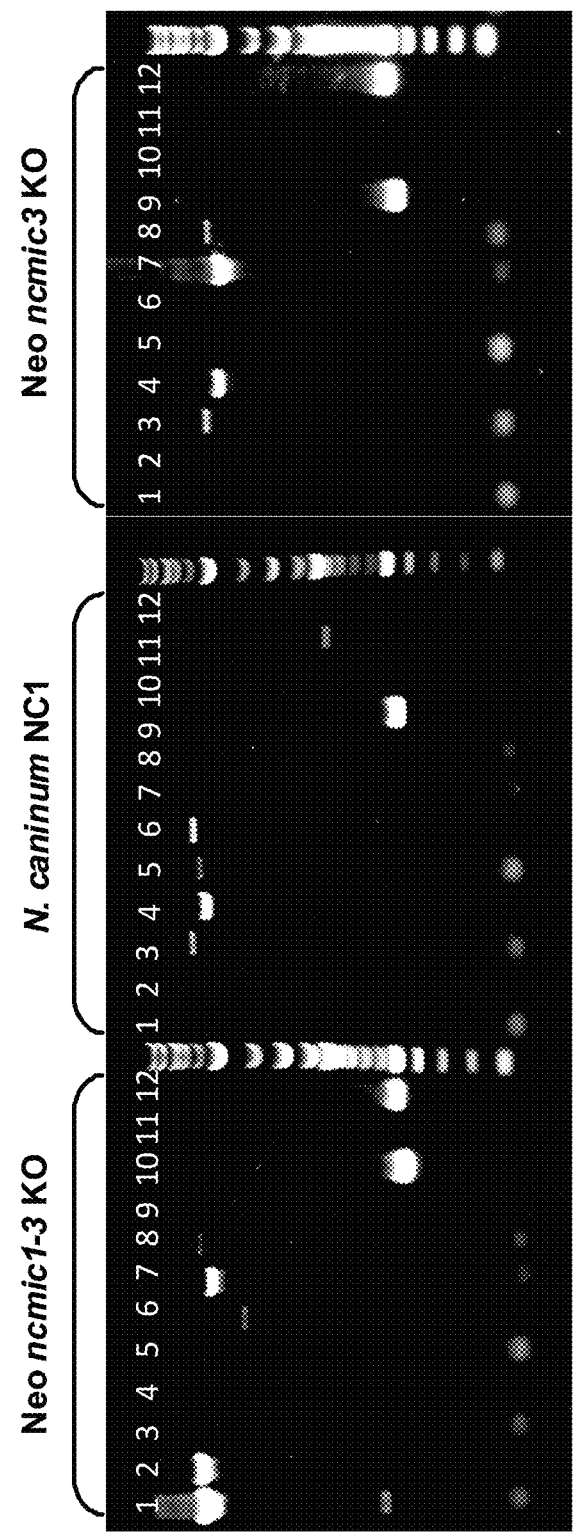

FIG. 5: this figure shows the electrophoretic profiles of the PCR products obtained respectively in the wild-type strain NC1 of *N. caninum*, in the mutant strain Neo ncmic3 KO and in the mutant strain Neo ncmic1-3 KO using the sets of PCR primers No. 1 to No. 12 in Table VII which correspond to SEQ ID NO: 7 to 16 and to SEQ ID NO: 21 to 30.

Figure 6:
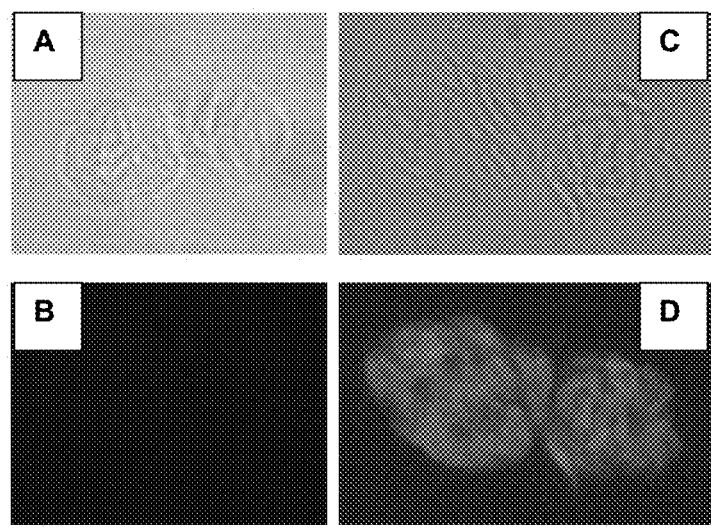

FIG. 6: this figure illustrates the analysis for detecting the protein GFP in the mutant strains Neo ncmic3 KO (images A and B) and Neo ncmic1-3 KO (images C and D) by immunofluorescence, using the fluorescent properties of the CAT-GFP protein. One and the same microscopic field is visualized in direct light (top images A and C) or in fluorescence (bottom images B and D).

Figure 7:
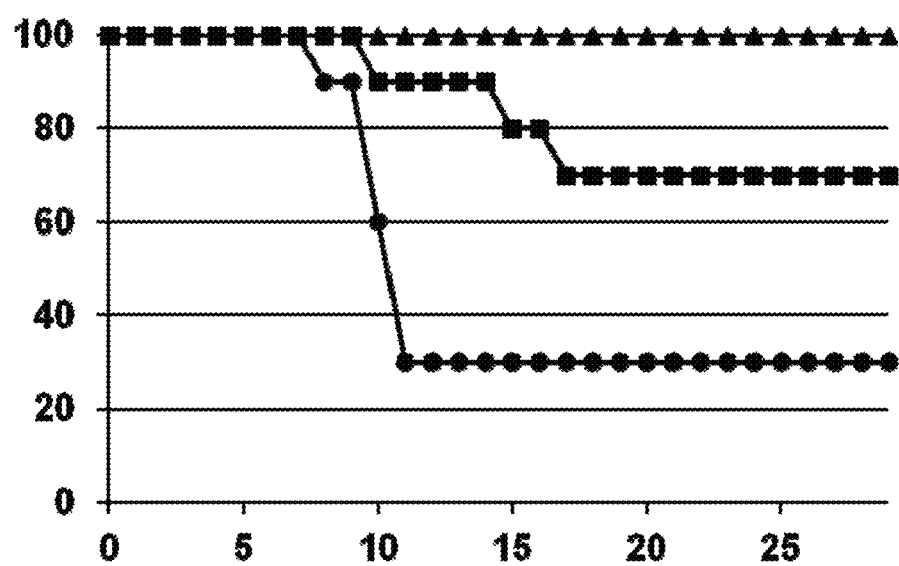

FIG. 7: this figure shows the percentage survival (on the y-axis) of female Balb/C mice infected by intraperitoneal route with $10^7$ tachyzoites of the wild-type strain NC1 of *Neospora caninum* (black circles) or mutant strains Neo ncmic3 KO (black squares) and Neo ncmic1-3 KO (black triangles). The x-axis shows the time elapsed after administering tachyzoites to the mice by injection (in days).

Figure 8:
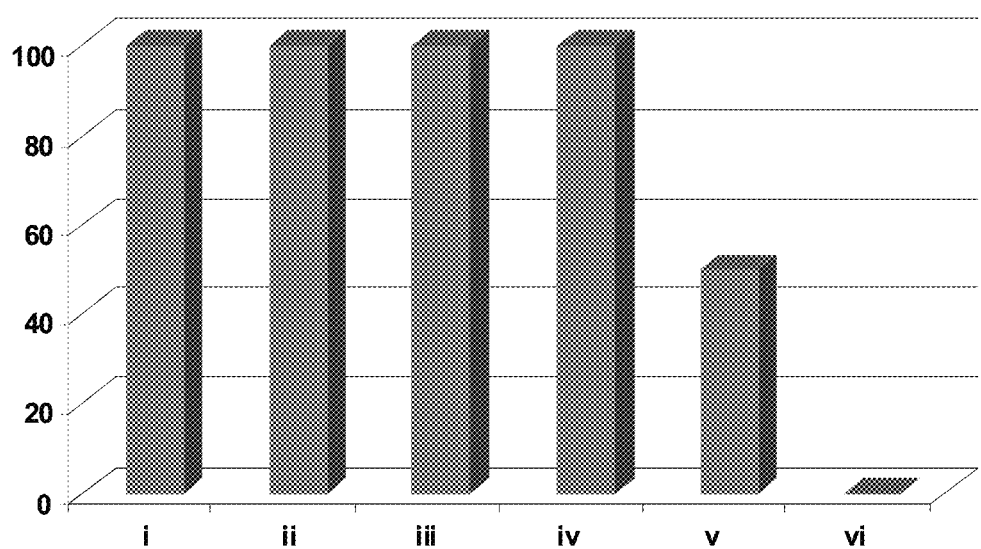
Figure 9:
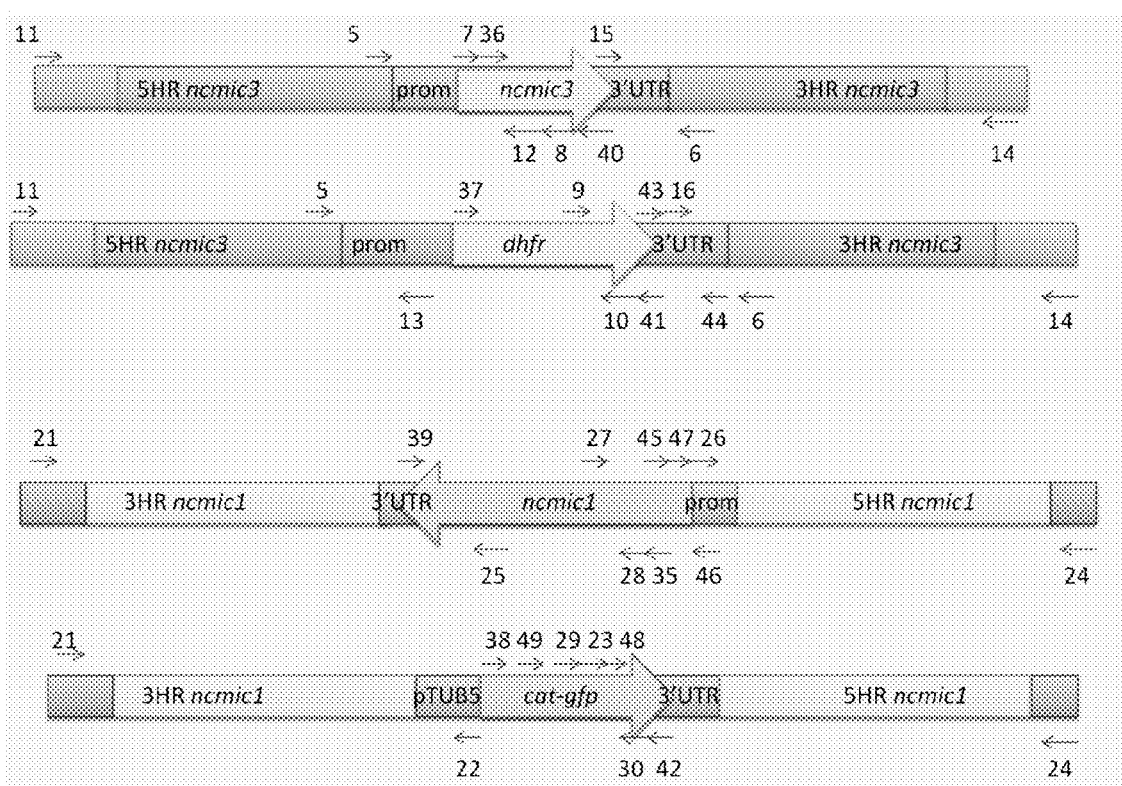

FIG. 8: this figure shows the percentage survival (on the y-axis) of female Balb/C mice after vaccination with increasing doses of the mutant strain ncmic1-3 KO and challenge 4 months post-vaccination, with a lethal dose of the wild-type strain NC1 of *Neospora caninum*. Six batches of mice are shown on the x-axis:

Batch i: the female Balb/C mice in this batch were vaccinated by intraperitoneal route with $5\times10^6$ tachyzoites of the mutant strain Neo ncmic1-3 KO and then challenged by intraperitoneal route with $2\times10^7$ tachyzoites of the wild-type strain NC1 of *Neospora caninum.*

Batch ii: the female Balb/C mice in this batch were vaccinated by intraperitoneal route with $10^7$ tachyzoites of the mutant strain Neo ncmic1-3 KO and then challenged by intraperitoneal route with $2\times10^7$ tachyzoites of the wild-type strain NC1 of *Neospora caninum.*

Batch iii: the female Balb/C mice in this batch were vaccinated by intraperitoneal route with a first dose of $10^7$ tachyzoites of the mutant strain Neo ncmic1-3 KO, and then a month later with a second dose of $10^7$ tachyzoites of the mutant strain Neo ncmic1-3 KO, and then challenged by intraperitoneal route with $2\times10^7$ tachyzoites of the wild-type strain NC1 of *Neospora caninum.*

Batch iv: the female Balb/C mice in this batch were vaccinated by intraperitoneal route with $5\times10^7$ tachyzoites of the mutant strain Neo ncmic1-3 KO and then challenged by intraperitoneal route with $2\times10^7$ tachyzoites of the wild-type strain NC1 of *Neospora caninum.*

Batch v: the female Balb/C mice in this batch were vaccinated by intraperitoneal route with $10^8$ tachyzoites of the mutant strain Neo ncmic1-3 KO and then challenged by intraperitoneal route with $2\times10^7$ tachyzoites of the wild-type strain NC1 of *Neospora caninum.*

Batch vi: the female Balb/C mice in this batch were not vaccinated with the tachyzoites of the mutant strain Neo ncmic1-3 KO but were challenged by intraperitoneal route with $2\times10^7$ tachyzoites of the wild-type strain NC1 of *Neospora caninum.*

FIG. 9: this figure illustrates the position of the nucleic acid primers used in the present invention for the detection of the presence of the four ncmic3, dhfr, ncmic1, cat-gfp genes in the wild-type strains and/or of the mutant strains of Neo ncmic1 KO and/or Neo ncmic3 KO and/or Neo ncmic1-3 KO of *Neospora caninum*. The numerals represent the numbering of the primer sequences defined in the present application.

FIG. 10: this figure shows the results of the ELISA tests carried out for assaying the anti-*N. caninum* IgG antibodies (optical density at 405 nm on the y-axis), present in the sera of the mice vaccinated 30 days previously with the strain Neo ncmic1-3 KO or unvaccinated. Four batches of mice are shown on the x-axis:

Batch i: the female mice in this batch were vaccinated with the tachyzoites of the mutant strain Neo ncmic1-3 KO.

Batch ii: the female mice in this batch were not vaccinated and are therefore naive with respect to neosporosis.

T+: a mouse infected by *N. caninum* and displaying anti-*N. caninum* IgG antibodies in its serum. This mouse serves as a positive control.

T−: a naive mouse that does not have anti-*N. caninum* IgG antibodies in its serum. This mouse serves as a negative control.

FIG. 11: this figure shows the results of the ELISA tests carried out for assaying the IgG1 (dark grey histogram) and IgG2A (light grey histogram) anti-*N. caninum* antibodies (optical density at 405 nm on the y-axis), present in the sera of the mice vaccinated 30 days previously with the strain Neo ncmic1-3 KO (12 mice included in this analysis) or not vaccinated (2 mice included in this analysis). Two batches of mice are shown on the x-axis:

Batch i: the female mice in this batch were vaccinated with the tachyzoites of the mutant strain Neo ncmic1-3 KO.

Batch ii: the female mice in this batch were not vaccinated and are therefore naive with respect to neosporosis.

FIG. 12-A: this figure shows the variation of mean rectal temperature in degrees Celsius (on the y-axis) of ewes from D-5 to D14 post-vaccination (on the x-axis). Four batches are shown in this figure:

Batch i: (broken grey curve-grey circles): the female sheep in this batch were not vaccinated with the tachyzoites of the mutant strain Neo ncmic1-3 KO but were fertilized, and then challenged at mid-gestation, by subcutaneous route with $10^7$ tachyzoites of the wild-type strain NC1 of *Neospora caninum.*

Batch ii (continuous black curve-black squares): the female sheep in this batch were vaccinated by subcutaneous route with a first dose of $10^7$ tachyzoites of the mutant strain Neo ncmic1-3 KO, and then a month later with a second dose of $10^7$ tachyzoites of the mutant strain Neo ncmic1-3 KO. The ewes were fertilized 2 months after the first vaccination, and then challenged, at mid-gestation, by subcutaneous route with $10^7$ tachyzoites of the wild-type strain NC1 of *Neospora caninum.*

Batch iii (continuous grey curve-grey triangles): the female sheep in this batch were vaccinated by subcutaneous route with a dose of $10^8$ tachyzoites of the mutant strain Neo ncmic1-3 KO. The ewes were fertilized 2 months after vaccination, and then challenged, at mid-gestation, by subcutaneous route with $10^7$ tachyzoites of the wild-type strain NC1 of *Neospora caninum*.

Batch iv (broken black curve-black crosses): the female sheep in this batch were not vaccinated with the tachyzoites of the mutant strain Neo ncmic1-3 KO and were not challenged with $10^7$ tachyzoites of the wild-type strain NC1 of *Neospora caninum*. They were fertilized at the same time as the ewes in batches (i), (ii) and (iii).

FIG. 12-B: this figure shows the variation of mean rectal temperature in degrees Celsius (on the y-axis) of the ewes from D-1 to D9 post-challenge (on the x-axis). Four batches are shown in this figure:

Batch i: (broken grey curve-grey circles): the female sheep in this batch were not vaccinated with the tachyzoites of the mutant strain Neo ncmic1-3 KO but were fertilized, and then challenged, at mid-gestation, by subcutaneous route with $10^7$ tachyzoites of the wild-type strain NC1 of *Neospora caninum*.

Batch ii (continuous black curve-black squares): the female sheep in this batch were vaccinated by subcutaneous route with a first dose of $10^7$ tachyzoites of the mutant strain Neo ncmic1-3 KO, and then a month later with a second dose of $10^7$ tachyzoites of the mutant strain Neo ncmic1-3 KO. The ewes were fertilized 2 months after the first vaccination, and then challenged, at mid-gestation, by subcutaneous route with $10^7$ tachyzoites of the wild-type strain NC1 of *Neospora caninum*.

Batch iii (continuous grey curve-grey triangles): the female sheep in this batch were vaccinated by subcutaneous route with a dose of $10^8$ tachyzoites of the mutant strain Neo ncmic1-3 KO. The ewes were fertilized 2 months after vaccination, and then challenged, at mid-gestation, by subcutaneous route with $10^7$ tachyzoites of the wild-type strain NC1 of *Neospora caninum*.

Batch iv (broken black curve-black crosses): the female sheep in this batch were not vaccinated with the tachyzoites of the mutant strain Neo ncmic1-3 KO and were not challenged with $10^7$ tachyzoites of the wild-type strain NC1 of *Neospora caninum*. They were fertilized at the same time as the ewes in batches (i), (ii) and (iii).

Figure 13:
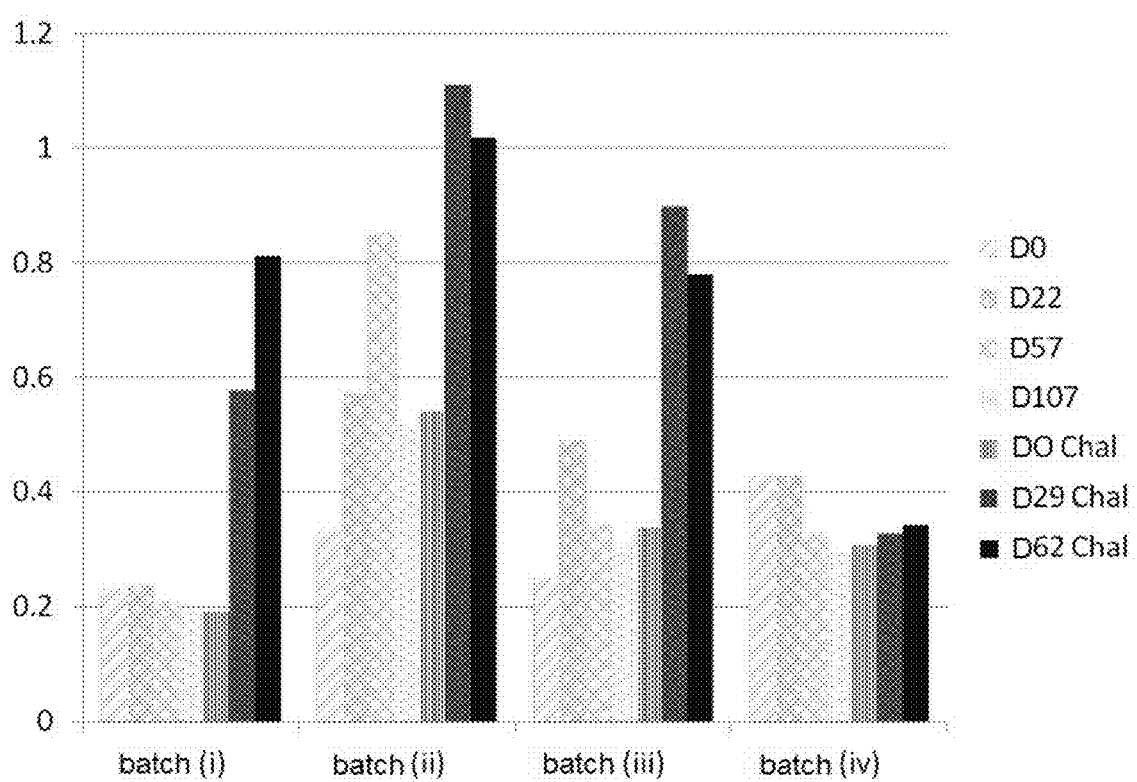

FIG. 13: this figure shows the mean values of the results of the ELISA tests (optical density at 405 nm on the y-axis), carried out with sera from the ewes on the day of vaccination of batch (ii) and (iii) (D0), on the day of boosting of batch (ii) (D22), 57 days after the first vaccination (D57), 107 days after the first vaccination (D107), on the day of challenge (D0 Chal), 29 days after challenge (D29 Chal) and 62 days after challenge (D62 Chal). Four batches are shown on the x-axis in this figure:

Batch i: the female sheep in this batch were not vaccinated with the tachyzoites of the mutant strain Neo ncmic1-3 KO but were fertilized, and then challenged at mid-gestation, by subcutaneous route with $10^7$ tachyzoites of the wild-type strain NC1 of *Neospora caninum*.

Batch ii: the female sheep in this batch were vaccinated by subcutaneous route with a first dose of $10^7$ tachyzoites of the mutant strain Neo ncmic1-3 KO, and then a month later with a second dose of $10^7$ tachyzoites of the mutant strain Neo ncmic1-3 KO. The ewes were fertilized 2 months after the first vaccination, and then challenged, at mid-gestation, by subcutaneous route with $10^7$ tachyzoites of the wild-type strain NC1 of *Neospora caninum*.

Batch iii: the female sheep in this batch were vaccinated by subcutaneous route with a dose of $10^8$ tachyzoites of the mutant strain Neo ncmic1-3 KO. The ewes were fertilized 2 months after vaccination, and then challenged, at mid-gestation, by subcutaneous route with $10^7$ tachyzoites of the wild-type strain NC1 of *Neospora caninum*.

Batch iv: the female sheep in this batch were not vaccinated with the tachyzoites of the mutant strain Neo ncmic1-3 KO and were not challenged with $10^7$ tachyzoites of the wild-type strain NC1 of *Neospora caninum*. They were fertilized at the same time as the ewes in batches (i), (ii) and (iii).

FIG. 14: this figure shows the electrophoretic profiles of the PCR products obtained respectively from the brains of mice infected by *Neospora caninum* or from the brains of mice vaccinated with the strain Neo ncmic3 KO, using the sets of PCR primers No. 1 (SEQ ID NO: 7 and SEQ ID NO: 8), No. 2 (SEQ ID NO: 9 and SEQ ID NO: 10), No. 3 (SEQ ID NO: 39 and SEQ ID NO: 25) or No. 4 (SEQ ID NO: 49 and SEQ ID NO: 42) defined in Table XVI.

EXAMPLES

In order to prepare the strain of *N. caninum* with the ncmic1 and ncmic3 genes knocked out, two steps of homologous recombination were carried out. The first step of homologous recombination makes it possible to obtain a simple mutant KO (strain Neo ncmic3 KO). The second step of homologous recombination is carried out in the strain Neo ncmic3 KO in order to obtain a doubly deleted strain (Neo ncmic1-3 KO) (FIG. 1).

Example 1

Construction of the Mutant Strain Neo Ncmic3 KO

The haploidy of the genome of *Neospora caninum* during the proliferative phase allows inactivation of a gene in a single homologous recombination.

All the tachyzoites of the strain NC1 of *Neospora caninum* used were produced in human fibroblasts (HFF) cultured in Dulbecco's minimum medium (DMEM) supplemented with 10% of foetal calf serum (FCS), 2 mM of glutamine, 50 U/mL of penicillin and 50 µg of streptomycin. They were harvested after mechanical lysis of the host cells and 3 passes through a 25G syringe.

a) Construction of the Plasmid pNcMic3KO-DHFR

The plasmid pNcMic3KO-DHFR (FIG. 2-A) contains the DHFR (dihydrofolate reductase) selection gene which confers resistance to pyrimethamine (Donald et al., PNAS, 1993, 90(24): 11703-11707). The DHFR selection gene is placed under the control of the tgdhfr promoter of *Toxoplasma gondii* (tgdhfr promoter) to allow expression of the gene in the parasite. The efficacy of this heterologous promoter had been demonstrated previously in *N. caninum*. This cassette is framed by the homologous regions (5HR-NcMic3 and 3HR-NcMic3) of the sequences flanking the ncmic3 gene. The DHFR selection cassette makes it possible to carry out selection for pyrimethamine.

The 5'UTR region of the ncmic3 gene was amplified by PCR from the genomic DNA of the strain NC1 of *Neospora caninum*. For the amplification, the primers 5 HR NCmic3 F KpnI and 5 HR NCmic3 R ClaI (SEQ ID NO: 1 and SEQ ID NO: 2) allow amplification of the 5'UTR region of the ncmic3 gene and creation of two restriction sites, which were used for cloning the 5HR fragment upstream of the DHFR selection cassette in the plasmid pT230 DHFR (KpnI at 5' and ClaI at 3' of the PCR fragment).

The 3'UTR region of the ncmic3 gene was amplified by PCR from the genomic DNA of the strain NC1 of *Neospora caninum*. For the amplification, the primers 3 HR NCmic3

F XbaI and 3 HR NCmic3 R NotI (SEQ ID NO: 3 and SEQ ID NO: 4) allow amplification of the 3'UTR region of the ncmic3 gene and creation of two restriction sites, which were used for cloning the 3HR fragment downstream of the DHFR selection cassette in the plasmid pT230 5HR-Nc-Mic3-DHFR (XbaI at 5' and NotI at 3' of the PCR fragment). The sequences of the primers are given in Table I below.

TABLE I

List of the primers used for integration of 5'UTR and 3'UTR sequences of the ncmic3 gene.

| Name of the primer | 5'→3' Sequence | No. of sequence |
|---|---|---|
| 5 HR NCmic3 F KpnI | CGC<u>GGTACC</u>CATGTGAATATGCTTTAACCGTGAC | SEQ ID NO: 1 |
| 5 HR NCmic3 R ClaI | CGC<u>ATCGAT</u>GAGCTATAACCCTTGGAAATGACTC | SEQ ID NO: 2 |
| 3 HR NCmic3 F XbaI | CGC<u>TCTAGA</u>CATGCTGATGAAGAAGGGAAGT | SEQ ID NO: 3 |
| 3 HR NCmic3 R NotI | CGC<u>GCGGCCGC</u>TCTCTCCTGAAGTCTTCGAGACC | SEQ ID NO: 4 |

The sequences of the restriction sites are underlined.

b) Conditions for Electroporation and Selection

50 μg of the plasmid pNcMic3KO-DHFR purified and then linearized by NotI was added to 5×10⁷NC1 tachyzoites of *Neospora caninum* suspended in the CYTOMIX electroporation medium containing ATP (3 mM) and glutathione (3 mM) (Van den Hoff et al., *Nucleic Acid Research*, June 11; 20(11): 2902), and electroporation was carried out in a cuvette with a 4-mm gap, in a volume of 800 μL on a BioRad apparatus (parameters: 2000 V, 50 ohms, 25 μF, with two electric shocks).

After electroporation, the tachyzoites were deposited on a monolayer of HFF cells in culture. For selection of the mutants, the culture medium is replaced and supplemented with the selection agent (2 μM pyrimethamine), 24 h after electroporation. Three culture passages are carried out in this medium.

After 16 days of selection, the resistant parasites are cloned by limit dilution in the wells of 96-well plates of HFF cells. After amplification, the lysis plaques caused by the parasite are investigated. The parasites are subcultured and their genomic DNA is extracted for PCR analyses. These PCR analyses should confirm integration of the transgene but should also allow differentiation of the parasites that have randomly integrated the transgene from the parasites of interest the ncmic3 gene of which has been effectively suppressed by homologous recombination.

c) PCR Analysis

Starting from the genomic DNA, PCRs were carried out for:

investigating the size of the DNA fragment amplified with a set of PCR primers No. 1: HR NCmic3 F (SEQ ID NO: 5) and HR NCmic3 R (SEQ ID NO: 6), present on the homologous sequences. With random integration of the transgene, two DNA fragments of 2163 bp and of 3824 bp are amplified, whereas with homologous recombination, only a fragment of 3824 bp is amplified. With the wild-type strains, only a fragment of 2163 bp is amplified.

verifying the presence/absence of the ncmic3 gene with the set of PCR primers No. 2: ORF NCmic3 F (SEQ ID NO: 7) and ORF NCmic3 R (SEQ ID NO: 8).

and/or verifying the presence/absence of the DHFR cassette with the set of PCR primers No. 3: ORF DHFR F (SEQ ID NO: 9) and ORF DHFR R (SEQ ID NO: 10).

The sequences of the primers and the size of the amplicons resulting from the different PCRs are shown in Table II and Table III below, respectively.

TABLE II

List of the primers used for the different PCRs for validation of the construction of the mutant strain Neo ncmic3 KO.

| Name of the primer | 5'→3' Sequence | No. of sequence | No. of PCR |
|---|---|---|---|
| HR NCmic3 F | GTCATCGACCGCCGGAACTAGTAGT | SEQ ID NO: 5 | 1 |
| HR NCmic3 R | GCAGAGGTTCTGCGTATCTAACACGG | SEQ ID NO: 6 | 1 |
| ORF NCmic3 F | TTTCCCTTCTAAACACAGTCG | SEQ ID NO: 7 | 2 |
| ORF NCmic3 R | CCTTCAGTGGTTCTCCATGAGT | SEQ ID NO: 8 | 2 |
| ORF DHFR F | CCTTCTCAGACAACGGGGTA | SEQ ID NO: 9 | 3 |
| ORF DHFR R | AGATCTTCACGCCCTTCTCA | SEQ ID NO: 10 | 3 |
| Integ NCmic3 F | GAAAGTGTCAGTGGTAGAGACTGC | SEQ ID NO: 11 | 4 and 6 |
| ORF NCmic3 R2 | CCTTCACTCGAGATCGCGCAAATGAGC | SEQ ID NO: 12 | 4 |
| ORF DHFR R2 | GGACCTCTGTACGAGACATGCCG | SEQ ID NO: 13 | 6 |
| Integ NCmic3 R | TGTTTACAGGTGATCCAGAAAAGG | SEQ ID NO: 14 | 5 and 7 |
| ORF NCmic3 F2 | GAATTTTGGGACAGGGGAAT | SEQ ID NO: 15 | 5 |
| ORF DHFR F2 | GTCTCTCGTTTTCCTCTCTTTTCGG | SEQ ID NO: 16 | 7 |

TABLE III

Size of the amplicons (in base pairs) of the different PCRs for validation of the construction of the mutant strain Neo ncmic3 KO.

| No. of PCR | Neo ncmic3 KO | *Neospora caninum* (NC1) |
|---|---|---|
| 1 | 3824 | 2163 |
| 2 | — | 850 |
| 3 | 504 | — |
| 4 | — | 3127 |
| 5 | — | 3374 |
| 6 | 2890 | — |
| 7 | 3258 | — |

The electrophoretic profiles of the PCR products are presented in FIG. 3-A. Among the clones studied, certain clones had a specific band of DHFR (PCR 3) but no specific band of ncmic3 (PCR 2). PCR No. 1 carried out on these clones revealed a band of 3824 bp specific for a Neo ncmic3 KO clone.

New PCR analyses were carried out on these clones of interest with new sets of primers. These PCRs, called integration PCRs, allow validation of the genetic KO using a primer present on the genome upstream or downstream of the sequences flanking the ncmic3 gene and a second primer present in the selection cassette (dhfr gene) or in the gene of interest (ncmic3) (FIG. 3-B).

In FIG. 3-B, PCRs No. 4 and No. 5 make it possible to show the presence of ncmic3 at the locus of ncmic3. PCR No. 4 is carried out with the primer set Integ NCmic3 F (SEQ ID NO: 11) and ORF NCmic3 R2 (SEQ ID NO: 12). PCR No. 5 is carried out with the primer set Integ NCmic3 R (SEQ ID NO: 14) and ORF NCmic3 F2 (SEQ ID NO: 15). The presence of bands for the wild-type strain NC1 of *Neospora caninum* and the absence of these bands for the mutant strain Neo ncmic3 KO are observed. In FIG. 3-B, PCRs No. 6 and No. 7 make it possible to show the presence of DHFR at the locus of ncmic3. PCR No. 6 is carried out with the primer set Integ NCmic3 (SEQ ID NO: 11) and ORF DHFR R2 (SEQ ID NO: 13). PCR No. 7 is carried out with the primer set Integ NCmic3 R (SEQ ID NO: 14) and ORF DHFR F2 (SEQ ID NO: 16). The absence of bands for the wild-type strain NC1 of *Neospora caninum* and the presence of bands for the Neo ncmic3 KO strain are noted. The presence of a non-specific band for PCR No. 6 at approximately 1000 bp should be noted.

All of the PCR results demonstrate that homologous recombination has indeed taken place and that the ncmic3 gene has indeed been deleted from the mutant strain Neo ncmic3 KO.

d) Analysis by Immunofluorescence

Analysis was carried out by immunofluorescence. 24 h before immunofluorescence analysis, 5×10⁵ parasites are deposited in a p24 well containing a coverslip covered with a HFF cell lawn.

The cells infected by the parasites are washed twice with 1×PBS and then fixed with paraformaldehyde (3.7% in 1×PBS) for 30 min. After 3 washings with 1×PBS, the cells are permeabilized with TRITON™ solution (0.1% in 1×PBS) for 5 minutes. (TRITON™ herein refers to TRITON™ X-100: 4-(1,1,3,3-Tetramethylbutyl)phenyl-polyethylene glycol, t-Octylphenoxypolyethoxyethanol, Polyethylene glycol tert-octylphenyl ether.) After 3 washings with 1×PBS, a saturation step is carried out with a solution of 1×PBS/10% FCS for 30 min. The cells are then incubated with the primary antibody diluted in a solution of PBS/2% FCS for 1 hour, washed 3 times and then incubated with the secondary antibody diluted in a solution of PBS/2% FCS for 1 hour. After 2 washings with 1×PBS, the coverslips are mounted on a slide with Immu-Mount and observed with a fluorescence microscope.

The primary antibody used is an antibody that allows detection of expression of the NcMIC3 protein in the parasite (primary antibody: rabbit anti-mic3 antibody and commercial secondary antibody: ALEXA FLUOR® 594 goat anti-rabbit, Life technologies ref. A-11012). ALEXA-FLUOR® 594 goat anti-rabbit is: Goat anti-Rabbit IgG (H+L) Secondary Antibody marked with ALEXA FLUOR® 594, which is shown below:

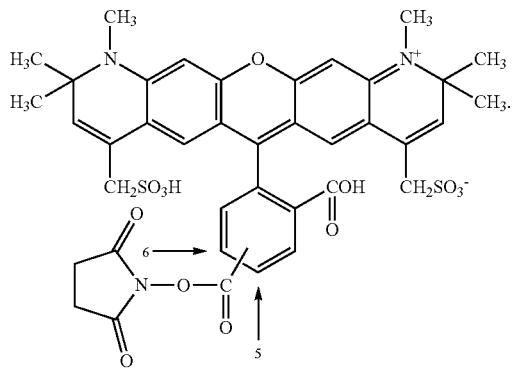

For the wild-type strain NC1 of *Neospora caninum*, red fluorescence is observed at the apical pole of the parasite, revealing the presence of the NcMIC3 protein (FIG. 4A), whereas for the mutant strain Neo ncmic3 KO, no fluorescence is observed at the apical pole of the parasite, demonstrating absence of the NcMIC3 protein (FIG. 4B).

Example 2

Construction of the Mutant Strain Neo Ncmic1 KO a) Construction of the Plasmid pNc mic1KO-CAT-GFP The plasmid pNcMic1KO-CAT-GFP (FIG. 2-B) contains a CAT-GFP selection cassette coding for a fusion protein giving both resistance to chloramphenicol (CAT) and a green fluorescence (GFP: Green Fluorescent Protein). The latter is placed under the control of the α-tubulin promoter of *Toxoplasma gondii* to allow expression of the gene in the parasite. Either side of the cassette, the homologous regions of the sequences flanking the ncmic1 gene have been cloned.

The 3'UTR region of the ncmic1 gene was amplified by PCR from the genomic DNA of the strain NC1 of *Neospora caninum*. For the amplification, the primers 3 HR NCmic1 F KpnI and 3 HR NCmic1 R HindIII (SEQ ID NO: 17 and SEQ ID NO: 18) allow amplification of the 3'UTR region of the ncmic1 gene and creation of two restriction sites, which were used for cloning the 3HR fragment upstream of the CAT-GFP selection cassette into the plasmid pT230 CAT-GFP (KpnI at 5' and HindIII at 3' of the PCR fragment). The 5'UTR region of the ncmic1 gene was amplified by PCR from the genomic DNA of the strain NC1 of *Neospora caninum*. For the amplification, the primers 5 HR NCmic1 F BamHI and 5 HR NCmic1 R NotI (SEQ ID NO: 19 and SEQ ID NO: 20) allow amplification of the 5'UTR region of the ncmic1 gene and creation of two restriction sites, which were used for cloning the 5HR fragment downstream of the CAT-GFP selection cassette into the plasmid pT230 3HRNcMic1CAT-GFP (BamHI at 5' and NotI at 3' of the PCR fragment). The sequences of the primers are given in Table IV below.

TABLE IV

List of the primers used for integration of the
5'UTR and 3'UTR sequences of the gene ncmic 1.

| Name of the primer | 5'→3' Sequence | No. of sequence |
|---|---|---|
| 3 HR NCmic1 F KpnI | CGCGGTACCAGGCAGAA GTAAAGAAGGTTCCTC | SEQ ID NO: 17 |
| 3 HR NCmic1 R HindIII | CGCAAGCTTTGATCACG CAAGAAAAGAAGC | SEQ ID NO: 18 |
| 5 HR NCmic1 F BamHI | CGCGGATCCCATTTGTA GATACGGTTGCACAC | SEQ ID NO: 19 |
| 5 HR NCmic1 R NotI | CGCGCGGCCGCACATTC AGACGGCAGAACTCTG | SEQ ID NO: 20 |

The sequences of the restriction sites are underlined.

b) Conditions for Electroporation and Selection

50 µg of the plasmid pNcMic1KO-CAT-GFP, purified and then linearized by KpnI, must be added to $5 \times 10^7$ NC1 tachyzoites suspended in CYTOMIX electroporation medium containing ATP (3 mM) and glutathione (3 mM) (Van den Hoff et al., *Nucleic Acid Research*, June 11; 20(11): 2902), and electroporation must be carried out in a cuvette with a 4-mm gap, in a volume of 800 µL on a BioRad apparatus (parameters: 2000 V, 50 ohms, 25 µF, with two electric shocks).

After electroporation, the tachyzoites will be deposited on a monolayer of HFF cells in culture. For selection of the mutant, the culture medium will be replaced and supplemented with the selection agent (50 µM chloramphenicol), 24 h after electroporation. Three culture passages must be carried out in this medium.

After 15 days of selection, the resistant parasites will be cloned by limit dilution in the wells of 96-well plates of HFF cells. After amplification, the lysis plaques caused by the parasite will be investigated. The parasites will be subcultured and their genomic DNA will be extracted for PCR analyses.

c) PCR Analysis

The sequences of the primers and the expected size of the amplicons resulting from the different PCRs are shown in Table V and Table VI below, respectively.

TABLE V

List of the primers used for the different
PCRs for validation of the construction
of the mutant strains Neo ncmic1 KO.

| Name of the primer | 5'→3' Sequence | No. of sequence | No. of PCR |
|---|---|---|---|
| Integ NCmic1 F | CCGAGCAAGTTAGC AAGTCC | SEQ ID NO: 21 | 1 and 3 |
| ORF CATGFP R | CCGTTTGGTGGATG TCTTCT | SEQ ID NO: 22 | 1 |
| ORF CATGFP F | GCATCGACTTCAAG GAGGAC | SEQ ID NO: 23 | 2 |
| Integ NCmic1 R | CTTGTCCGTCACAT CGTTTG | SEQ ID NO: 24 | 2 and 4 |
| ORF NCmic1 R | TTCTCCAGGCACTC ACCTCT | SEQ ID NO: 25 | 3 |
| ORF NCmic1 F | AGCTTCCAACAACG AGAGGA | SEQ ID NO: 26 | 4 |

TABLE V -continued

List of the primers used for the different
PCRs for validation of the construction
of the mutant strains Neo ncmic1 KO.

| Name of the primer | 5'→3' Sequence | No. of sequence | No. of PCR |
|---|---|---|---|
| ORF NCmic1 F2 | CCCAGGATATCGTT TGTTGC | SEQ ID NO: 27 | 5 |
| ORF NCmic1 R2 | CTTCTGATGCACGG AACTGA | SEQ ID NO: 28 | 5 |
| ORF CATGFP F2 | CCTGAAGTTCATCT GCACCA | SEQ ID NO: 29 | 6 |
| ORFCATGFP R2 | GTAGTGGTTGTCGG GCAGCA | SEQ ID NO: 30 | 6 |

TABLE VI

Size of the amplicons (in base pairs) of
the different PCRs for validation
of the construction of the mutant
strain Neo ncmic1 KO.

| No. of PCR | Neo ncmic1KO | *Neospora caninum* (NC1) |
|---|---|---|
| 1 | 3359 | — |
| 2 | 3421 | — |
| 3 | — | 3746 |
| 4 | — | 3046 |
| 5 | — | 449 |
| 6 | 472 | — |

Example 3

Construction of the Mutant Strain Neo Ncmic1-3 KO a) Construction of the Plasmid pNc Mic1KO CAT-GFP The construction of the plasmid pNcMic1KO-CAT-GFP is described in Example 2 (2a).

b) Conditions for Electroporation and Selection

50 µg of the plasmid pNcMic1KO-CAT-GFP, purified and then linearized by KpnI, was added to $5 \times 10^7$ Neo ncmic3 KO tachyzoites suspended in the CYTOMIX electroporation medium containing ATP (3 mM) and glutathione (3 mM) (Van den Hoff et al., *Nucleic Acid Research*, June 11; 20(11): 2902), and electroporation was carried out in a cuvette with a 4-mm gap, in a volume of 800 µL on a BioRad apparatus (parameters: 2000 V, 50 ohms, 25 µF, with two electric shocks).

After electroporation, the tachyzoites were deposited on a monolayer of HFF cells in culture. For selection of the mutants, the culture medium is replaced and supplemented with the selection agent (chloramphenicol 50 µM), 24 h after electroporation. Three culture passages are carried out in this medium.

After 15 days of selection, the resistant parasites are cloned by limit dilution in the wells of 96-well plates of HFF cells. After amplification, the lysis plaques caused by the parasite are investigated. The parasites are subcultured and their genomic DNA is extracted for PCR analyses.

c) PCR Analysis

The sequences of the primers and the size of the amplicons resulting from the different PCRs are shown in Table VII and Table VIII below, respectively.

TABLE VII

List of the primers used for the different PCRs for validation of the construction of the mutant strains Neo ncmic3 KO and Neo ncmic1-3 KO.

| Name of the primer | 5'→3' Sequence | No. of sequence | No. of PCR |
|---|---|---|---|
| Integ NCmic1 F | CCGAGCAAGTTAGCAAGTCC | SEQ ID NO: 21 | 1 and 3 |
| ORF CATGFP R | CCGTTTGGTGGATGTCTTCT | SEQ ID NO: 22 | 1 |
| ORF CATGFP F | GCATCGACTTCAAGGAGGAC | SEQ ID NO: 23 | 2 |
| Integ NCmic1 R | CTTGTCCGTCACATCGTTTG | SEQ ID NO: 24 | 2 and 4 |
| ORF NCmic1 R | TTCTCCAGGCACTCACCTCT | SEQ ID NO: 25 | 3 |
| ORF NCmic1 F | AGCTTCCAACAACGAGAGGA | SEQ ID NO: 26 | 4 |
| Integ NCmic3 F | GAAAGTGTCAGTGGTAGAGACTGC | SEQ ID NO: 11 | 5 and 7 |
| ORF NCmic3 R2 | CCTTCACTCGAGATCGCGCAAATGAGC | SEQ ID NO: 12 | 5 |
| ORF DHFR R2 | GGACCTCTGTACGAGACATGCCG | SEQ ID NO: 13 | 7 |
| Integ NCmic3 R | TGTTTACAGGTGATCCAGAAAAGG | SEQ ID NO: 14 | 6 and 8 |
| ORF NCmic3 F2 | GAATTTTGGGACAGGGGAAT | SEQ ID NO: 15 | 6 |
| ORF DHFR F2 | GTCTCTCGTTTTCCTCTCTTTTCGG | SEQ ID NO: 16 | 8 |
| ORF NCmic1 F2 | CCCAGGATATCGTTTGTTGC | SEQ ID NO: 27 | 9 |
| ORF NCmic1 R2 | CTTCTGATGCACGGAACTGA | SEQ ID NO: 28 | 9 |
| ORF CATGFP F2 | CCTGAAGTTCATCTGCACCA | SEQ ID NO: 29 | 10 |
| ORFCATGFP R2 | GTAGTGGTTGTCGGGCAGCA | SEQ ID NO: 30 | 10 |
| ORF NCmic3 F | TTTCCCTTCTAAACACAGTCG | SEQ ID NO: 7 | 11 |
| ORF NCmic3 R | CCTTCAGTGGTTCTCCATGAGT | SEQ ID NO: 8 | 11 |
| ORF DHFR F | CCTTCTCAGACAACGGGGTA | SEQ ID NO: 9 | 12 |
| ORF DHFR R | AGATCTTCACGCCCTTCTCA | SEQ ID NO: 10 | 12 |

TABLE VIII

Size of the amplicons (in base pairs) of the different PCRs for validation of the construction of the mutant strains Neo ncmic3 KO and Neo ncmic1-3 KO.

| No. of PCR | Neo ncmic1-3 KO | *Neospora caninum* (NC1) | Neo ncmic3 KO |
|---|---|---|---|
| 1 | 3359 | — | — |
| 2 | 3421 | — | — |
| 3 | — | 3746 | 3746 |
| 4 | — | 3046 | 3046 |
| 5 | — | 3127 | — |
| 6 | — | 3374 | — |
| 7 | 2890 | — | 2890 |
| 8 | 3258 | — | 3258 |
| 9 | — | 449 | 449 |
| 10 | 472 | — | — |
| 11 | — | 850 | — |
| 12 | 504 | — | 504 |

In FIG. 5, PCR No. 1 is carried out with the set of primers Integ NCmic1 F (SEQ ID NO: 21) and ORF CATGFP R (SEQ ID NO: 22). PCR 2 is carried out with the set of primers ORF CATGFP F (SEQ ID NO: 23) and Integ NCmic1 R (SEQ ID NO: 24). PCR No. 3 is carried out with the set of primers Integ NCmic1 F (SEQ ID NO: 21) and ORF NCmic1 R (SEQ ID NO: 25). PCR No. 4 is carried out with the set of primers Integ NCmic1 R (SEQ ID NO: 24) and ORF NCmic1 F (SEQ ID NO: 26). PCR No. 5 is carried out with the set of primers Integ NCmic3 F (SEQ ID NO: 11) and ORF NCmic3 R2 (SEQ ID NO: 12). PCR No. 6 is carried out with the set of primers Integ NCmic3 R (SEQ ID NO: 14) and ORF NCmic3 F2 (SEQ ID NO: 15). PCR No. 7 is carried out with the set of primers Integ NCmic3 F (SEQ ID NO: 11) and ORF DHFR R2 (SEQ ID NO: 13). PCR No. 8 is carried out with the set of primers Integ NCmic3 R (SEQ ID NO: 14) and ORF DHFR F2 (SEQ ID NO: 16). PCR No. 9 is carried out with the set of primers ORF NCmic1 F2 (SEQ ID NO: 27) and ORF NCmic1 R2 (SEQ ID NO: 28). PCR No. 10 is carried out with the set of primers ORF CATGFP F2 (SEQ ID NO: 29) and ORF CATGFP R2 (SEQ ID NO: 30). PCR No. 11 is carried out with the set of primers ORF NCmic3 F (SEQ ID NO: 7) and ORF NCmic3 R (SEQ ID NO: 8). PCR No. 12 is carried out with the set of primers ORF DHFR F (SEQ ID NO: 9) and ORF DHFR R (SEQ ID NO: 10).

The electrophoretic analyses of the PCR products show that the strain Neo ncmic1-3 KO no longer has the ncmic1 and ncmic3 genes (wells 3, 4, 5, 6, 9 and 11, FIG. 5) but does have the dhfr and cat-gfp genes (wells 1, 2, 7, 8, 10 and 12, FIG. 5), thus validating production of the strain Neo ncmic1-3 KO. All of the PCR results demonstrate that homologous recombination has indeed taken place and the ncmic1 and ncmic3 genes have indeed been deleted from the strain Neo ncmic1-3 KO.

d) Immunofluorescence Analysis

Immunofluorescence analysis was carried out solely by direct observation of the fluorescence of the parasite (FIG. 6).

The parasites of the two mutant strains are visualized in direct light (images A and C). One and the same microscopic field is visualized in fluorescence. Green fluorescence, due to expression of the recombinant chimeric protein CAT-GFP, is only detected in the mutant strain Neo ncmic1-3 KO (image D) following insertion of the CAT-GFP cassette. Conversely, the strain Neo ncmic3 KO, which does not have a CAT-GFP cassette, does not express the CAT-GFP protein and consequently does not display fluorescence (image B).

Example 4

Effects of the Inactivation of the NcMIC3 Protein or the NcMIC1 and NcMIC3 Proteins on the Infectious Properties of *Neospora caninum*

The mutant strains Neo ncmic3 KO and Neo ncmic1-3 KO described in Examples 1 and 3 were maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

Between 60 and 80% of the female Balb/C mice generally die between 8 and 11 days after being infected by intraperitoneal route with $10^7$ tachyzoites of the strain NC1 of *Neospora caninum*.

The virulence of the mutants Neo ncmic3 KO and Neo ncmic1-3 KO was investigated on a minimum batch of 10 female Balb/C mice by intraperitoneal injection of $10^7$ tachyzoites/mouse. The controls were carried out under the same conditions on batches of 10 female Balb/C mice using the strain NC1 of *Neospora caninum*.

FIG. 7 shows that 70% of the mice infected with $10^7$ tachyzoites of the strain NC1 of *Neospora caninum* are dead 11 days after infection (black circles). The mice infected with the mutant strain Neo ncmic3 KO (black squares) display a delay in mortality (death of the mice between 9 days and 17 days after infection) and a significant attenuation of the virulence of the parasite (30% mortality as against 70% with the wild-type strain 29 days after infection). Moreover, in the case of the mice infected with the mutant strain Neo ncmic1-3 KO (black triangles), 100% survival is observed 29 days after infection.

The mice were also infected with increasing quantities of the strain NC1 of *Neospora caninum* and the mutant strains Neo ncmic3 KO and Neo ncmic1-3 KO. The dose required for 50% mortality ($LD_{50}$) is $6 \times 10^6$ tachyzoites for the wild-type strain NC1 of *Neospora caninum* and $22 \times 10^6$ tachyzoites for the strain Neo ncmic3 KO. For the strain Neo ncmic1-3 KO, the $LD_{50}$ is very much higher than $10^8$ tachyzoites, i.e. 17 times the $LD_{50}$ of the wild-type strain NC1 of *Neospora caninum*. In fact, no mortality is observed at this dose with the mutant strain Neo ncmic1-3 KO.

Example 5

Efficacy of the Strain Neo Ncmic1-3 KO in the Prevention of Neosporosis in a Murine Model of Lethal Neosporosis The mutant strain Neo ncmic1-3 KO described in Example 3 was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

Female Balb/C mice were divided into 6 separate batches: (i) a batch vaccinated by intraperitoneal route with $5 \times 10^6$ tachyzoites of the mutant strain Neo ncmic1-3 KO, (ii) a batch vaccinated by intraperitoneal route with $10^7$ tachyzoites of the mutant strain Neo ncmic1-3 KO, (iii) a batch vaccinated by intraperitoneal route with $10^7$ tachyzoites of the mutant strain Neo ncmic1-3 KO and boosted 1 month after the first injection with $10^7$ tachyzoites of the mutant strain Neo ncmic1-3 KO, (iv) a batch vaccinated by intraperitoneal route with $5 \times 10^7$ tachyzoites of the mutant strain Neo ncmic1-3 KO, (v) a batch vaccinated by intraperitoneal route with $10^8$ tachyzoites of the mutant strain Neo ncmic1-3 KO and (vi) an unvaccinated control batch.

Four months after vaccination, all the mice were challenged by intraperitoneal route with $2 \times 10^7$ tachyzoites of the wild-type strain NC1 of *Neospora caninum*. The wild-type strain NC1 of *Neospora caninum* was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20. The dose used for challenge is sufficient to lead to 100% mortality of the challenged mice. The survival of the mice is then monitored for one month.

FIG. 8 shows that the vaccinated mice in batches (i) to (iv) are completely protected from a reinfection by a virulent wild strain NC1 of *Neospora caninum* causing 100% mortality of the mice in the control batch (vi), all of which die on the 6th day after challenge. The mice vaccinated with the higher dose of the strain Neo ncmic1-3 KO (batch (v)) display intermediate mortality (50%). In contrast to the mice in the control batch (vi), the mortality of the mice in this batch occurs earlier (4.5 days on average). This observation might be explained by a strong inflammatory response generated by this group of mice at the time of challenge.

Example 6

Efficacy of the Mutant Strain Neo Ncmic1-3 KO in the Prevention of Neosporosis in a Murine Model of Congenital Neosporosis—Experiment 1

The mutant strain Neo ncmic1-3 KO described in Example 3 was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

Female OF1 mice were divided into 2 separate batches: (i) a batch vaccinated by intraperitoneal route with $10^7$ tachyzoites of the mutant strain Neo ncmic1-3 KO, (ii) an unvaccinated control batch.

Two months after vaccination, the mice were mated (D0) at a rate of three female mice to one male. The pregnant mice are diagnosed by weighing and on the tenth day of gestation are subjected to infectious challenge by intraperitoneal route with $2 \times 10^6$ tachyzoites of the wild-type strain NC1 of *Neospora caninum*. The wild-type strain NC1 of *Neospora caninum* was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

One day before parturition, the female mice were sacrificed. The placentas and the foetuses were isolated and the DNA was extracted. A nested PCR is carried out from the region of the NC5 gene of *N. caninum* (Yamage et al., J. Parasitol. 1996 April 82(2): 272-9, Baszler et al., J Clin Microbiol, 1999 December, 37(12): 4059-64). The primer pair NC5 FA (SEQ ID NO: 31) and NC5 RA (SEQ ID NO: 32) is used for the primary PCR, and the primer pair NC5 FB (SEQ ID NO: 33) and NC5 RB (SEQ ID NO: 34) is used for the secondary PCR. The sequences of the primers are given in Table IX below.

TABLE IX

List of the primers used for the PCRs for investigating for the presence of the parasite *N. caninum* in the tissues.

| Name of the primer | 5'→3' Sequence | | | No. of PCR |
|---|---|---|---|---|
| NC5 FA | CCCAGTGCGTCCAA TCCTGTAAC | SEQ ID NO: | 31 | Primary |
| NC5 RA | CTCGCCAGTCAACC TACGTCTTCT | SEQ ID NO: | 32 | Primary |
| NC5 FB | TAATCTCCCCCGTC ATCAGT | SEQ ID NO: | 33 | Secondary |
| NC5 RB | GGGTGAACCGAGGG AGTTG | SEQ ID NO: | 34 | Secondary |

For each placenta and foetus, three independent PCRs are carried out. The placentas and foetuses are considered positive when *Neospora caninum* is detected in the case of at least one PCR. The results are presented in Table X below.

TABLE X

Investigation for *Neospora caninum* in the placental and foetal tissues of mice vaccinated with the strain Neo ncmic1-3 KO and challenged with the wild-type strain NC1 (batch (i)) in comparison with unvaccinated control mice, challenged with the wild-type strain NC1 (batch (ii)).

| Batch (i) Mice vaccinated with $10^7$ tachyzoites of | Investigation for *Neospora caninum* in the placentas | | |
|---|---|---|---|
| | Number of placentas investigated | Number of positive placentas | % of positive placentas |
| | 106 | 47 | 44.3% |

TABLE X-continued

Investigation for *Neospora caninum* in the placental and foetal tissues of mice vaccinated with the strain Neo ncmic1-3 KO and challenged with the wild-type strain NC1 (batch (i)) in comparison with unvaccinated control mice, challenged with the wild-type strain NC1 (batch (ii)).

| the strain Neo ncmic1-3 KO and challenged with $2.10^6$ tachyzoite of the wild-type strain NC1 | Investigation for *Neospora caninum* in the foetuses | | |
|---|---|---|---|
| | Number of foetuses investigated | Number of positive foetuses | % of positive foetuses |
| | 109 | 23 | 21.1% |
| Batch (ii) Unvaccinated mice, challenged with $2.10^6$ tachyzoites of the wild-type strain NC1 | Investigation for *Neospora caninum* in the placentas | | |
| | Number of placentas investigated | Number of positive placentas | % of positive placentas |
| | 37 | 37 | 100% |
| | Investigation for *Neospora caninum* in the foetuses | | |
| | Number of foetuses investigated | Number of positive foetuses | % of positive foetuses |
| | 36 | 27 | 75% |

These results demonstrate that vaccination with the attenuated mutant strain Neo ncmic1-3 KO considerably reduces the maternal-foetal transmission of the parasite, thus validating the efficacy of the strain Neo ncmic1-3 KO for preventing harmful effects of neosporosis in a murine model of endogenous congenital neosporosis.

Example 7

Efficacy of the Mutant Strain Neo Ncmic1-3 KO in the Prevention of Neosporosis in an Ovine Model of Congenital Neosporosis a) Experimental Procedure The mutant strain Neo ncmic1-3 KO described in Example 3 was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

Romanov ewes seronegative for *Neospora caninum* and *Toxoplasma gondii* were divided into 4 separate batches: a batch comprising 14 control ewes not vaccinated with the mutant strain Neo ncmic1-3 KO, challenged by subcutaneous route with $10^7$ tachyzoites of the wild-type strain NC1 of *Neospora caninum* (batch i), a batch comprising 15 ewes vaccinated by subcutaneous route with $10^7$ tachyzoites of the mutant strain Neo ncmic1-3 KO and then boosted by subcutaneous route, 1 month after the first injection, with $10^7$ tachyzoites of the mutant strain Neo ncmic1-3 KO and challenged by subcutaneous route with $10^7$ tachyzoites of the wild-type strain NC1 of *Neospora caninum* (batch ii), a batch comprising 14 ewes vaccinated by subcutaneous route with $10^8$ tachyzoites of the mutant strain Neo ncmic1-3 KO and challenged by subcutaneous route with $10^7$ tachyzoites of the wild-type strain NC1 of *Neospora caninum* (batch iii) and a batch comprising 5 control ewes not vaccinated with the mutant strain Neo ncmic1-3 KO and not challenged with the wild-type strain NC1 of *Neospora caninum* (batch iv).

Two months after the first vaccination, the ewes were artificially inseminated. They were returned to the ram 3 weeks after artificial insemination. Ultrasonography was then carried out and led to the diagnosis that 14 ewes out of 14 were pregnant in batch (i), 13 ewes out of 15 in batch (ii), 13 ewes out of 14 in batch (iii) and 4 ewes out of 5 in batch (iv).

The pregnant ewes in batches (i), (ii) and (iii) were subjected at mid-gestation to infectious challenge with $10^7$ tachyzoites of the wild-type strain NC1 of *Neospora caninum*. The wild-type strain NC1 of *Neospora caninum* was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

b) Temperature Recorded Post-Immunization and Post-Challenge

From 5 days before vaccination to 14 days post-vaccination, the rectal temperatures of the ewes were recorded daily. The mean values of the temperatures post-immunization of batches (i), (ii), (iii) and (iv) are presented in FIG. 12-A. The temperatures of the control batches (iii) and (iv) remain physiological. In contrast, a temperature peak is observed for the two vaccinated batches (>39.5° C.). A return to physiological temperatures is observed 5 days after immunization.

On the day before infection and during the subsequent days, the rectal temperature was recorded daily. The mean values of the temperatures post-infection of batches (i), (ii), (iii) and (iv) are presented in FIG. 12-B. The temperatures of the control batch (iv) remain physiological. In contrast, a temperature peak is observed for the vaccinated batches (i), (ii) and (iii). For the control batch that was only infected (batch (i)), the febrile peak lasted 3 days with a maximum at 40° C. on D3. For the vaccinated batches (ii) and (iii), the febrile peak occurs starting from D2, lasts for only two days and is less intense (39.5° C.).

c) Analysis of the Humoral Immune Response

The immune response was investigated post-immunization and post-challenge, using ELISA for evaluating the kinetics of appearance of the specific anti-*N. caninum* IgGs in the serum of the ewes in batches (i), (ii), (iii) and (iv). The sera are taken before immunization (D0) and then on D22, D57 and D107 post-vaccination and finally after challenge (D0 Chal, D29 Chal, D62 Chal). The blood is taken from the jugular vein and the sample is left overnight at 4° C. for clot formation. The serum is recovered by centrifuging the samples at 5000 g for 10 min. The supernatant is recovered and stored at −20° C.

In order to analyse the humoral immune response induced after the vaccination, an extract of *N. caninum* is prepared. For the preparation of this total parasite extract, the tachyzoites of the strain NC-1 are washed, sonicated twice at 60 W/s for 10 min in ice and centrifuged at 2000 g for 30 minutes at +4° C. The supernatant is recovered and the concentration is determined by BCA assay, which uses bovine serum albumin (BSA) as standard. The aliquots are stored at −80° C. until used.

The total parasite extract of the strain NC1 is diluted in a carbonate buffer, pH 9.6, in order to obtain a final concentration of 10 µg/mL. The plates are then washed three times with the washing buffer (1×PBS—0.05% TWEEN® 20, which is Polyethylene glycol sorbitan monolaurate, Polyoxyethylenesorbitan monolaurate) and then saturated for 1.5 h at 37° C. with a solution of 1×PBS—0.05% TWEEN® 20 supplemented with 4% of bovine serum albumin (BSA) (Sigma). The medium is then removed. The sera to be tested are diluted to 1/50th in a solution of 1×PBS—0.05% TWEEN® 20 and are deposited in duplicate in the wells. After incubation for 1 hour at 37° C. and a new series of washings, anti-sheep IgG secondary antibody coupled to alkaline phosphatase (Jackson ImmunoResearch 713-055_147, donkey anti-Sheep IgG) and diluted to 1/5000th is deposited at a rate of 100 µL per well. The samples are then incubated for one hour at 37° C. After a new series of three washings, the detection is carried out by the addition of 100 µL of a solution of disodium paranitrophenylphosphate (PnPP) (Sigma) at 1 mg/mL, in DEA-HCl buffer, to each well. After incubation for 20 min at ambient temperature, away from the light, the absorbance at 405 nm is measured using a plate reader (Multiskan MCC340 Wallace). The mean values of the results of the ELISA tests on D0, D22, D57 and D107 post-immunization and on D0, D29, D62 post-challenge for the sera from the different batches of ewes diluted to 1/50th are shown in FIG. 13.

After immunization, the unvaccinated ewes in control batches (i) and (iv) did not develop a humoral response. However, the ewes in batches (ii) and (iii) developed an anti-neosporosis IgG response starting from D22. This IgG response is boosted at the second vaccination of batch (ii). It then decreases for the two batches (ii) and (iii).

After challenge, the unchallenged ewes in control batch (iv) did not develop a humoral response. However, the ewes in batches (i), (ii) and (iii) developed an anti-neosporosis IgG response. The humoral response of the vaccinated batches (ii) and (iii) is more rapid than for the unvaccinated batch (i).

d) Investigation of Abortions

After challenge, the ewes were monitored daily until parturition and the abortions and stillbirths were recorded.

The results of this study are presented in Table XV below.

| Batches | Number of lambs expected (%) | Number of abortions (%) | Number of stillbirths (%) | Number of live lambs (%) |
|---|---|---|---|---|
| (i) (unvaccinated/infected) | 35 (100%) | 29 (82.9%) | 1 (2.8%) | 5 (2.8%) |
| (ii) (vaccinated then boosted with $10^7$ tachyzoites and then infected) | 38 (100%) | 0 (0%) | 11 (29%) | 27 (71%) |
| (iii) (vaccinated with $10^8$ tachyzoites and then infected) | 33 (100%) | 3 (9.1%) | 8 (24.2%) | 22 (66.6%) |
| (iv) (unvaccinated/not infected) | 13 (100%) | 0 (0%) | 1 (7.7%) | 12 (92.3%) |

These results demonstrate that vaccination with the attenuated mutant strain Neo ncmic1-3 KO considerably reduces the harmful effects of an infection of a ruminant, in particular an ovine, with *Neospora caninum*.

Example 8

Analysis of the Humoral Immune Response Following Vaccination with the Strain Neo Ncmic1-3 KO The mutant strain Neo ncmic1-3 KO described in Example 3 was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

Female OF1 mice were divided into 2 separate batches: (i) a batch vaccinated by intraperitoneal route with $5\cdot10^7$ tachyzoites of the mutant strain Neo ncmic1-3 KO, (ii) a control batch, unvaccinated but challenged.

One month after vaccination, a submaxillary blood sample is taken. The whole blood is stored for 2 hours at 37° C. before being centrifuged at 5000 g for 10 minutes in order to store the serum. The serum is stored at −20° C. until used.

In order to analyse the humoral immune response induced after vaccination, an extract of *N. caninum* is prepared. For the preparation of this total parasite extract, the tachyzoites of the strain NC-1 are washed, sonicated twice at 60 W/s for 10 min in ice and centrifuged at 2000 g for 30 minutes at +4° C. The supernatant is recovered and the concentration is determined by BCA assay, which uses bovine serum albumin (BSA) as standard. The aliquots are stored at −80° C. until used.

Using sera from mice vaccinated with the mutant strain Neo ncmic1-3 KO and from unvaccinated mice, ELISA tests are carried out in order to characterize the humoral immune response induced by the mutant strain Neo ncmic1-3 KO.

a) Investigation for the Total IgGs Specific to *N. caninum*

Figure 10:
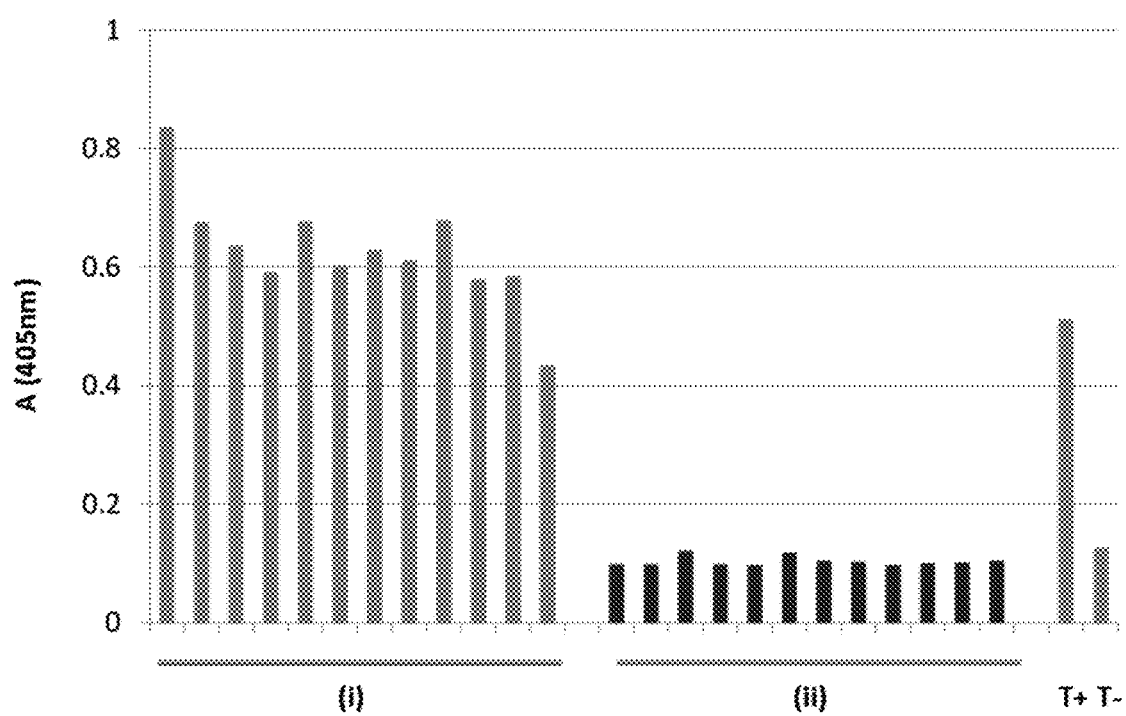

The total parasite extract of the strain NC1 is diluted in a carbonate buffer, pH 9.6, in order to obtain a final concentration of 10 µg/mL. 96-well plates with flat-bottomed wells are then sensitized overnight at +4° C. by depositing 100 µL of total extract of *N. caninum* in each well. The plates are then washed three times with the washing buffer (1×PBS—0.05% TWEEN® 20) and then saturated for 1.5 h at 37° C. with a solution of 1×PBS—0.05% TWEEN® 20 supplemented with 4% of bovine serum albumin (BSA) (Sigma). The medium is then removed. The sera to be tested are diluted to 1/50th in a solution of 1×PBS—0.05% TWEEN® 20 and are deposited in duplicate in the wells. After incubation for 1 hour at 37° C. and a new series of washings, anti-mouse IgG secondary antibody coupled to alkaline phosphatase (Sigma A3562, goat anti-Mouse IgG) and diluted to 1/5000th is deposited at a rate of 100 µL per well. The samples are then incubated for one hour at 37° C. After a new series of three washings, the detection is carried out by the addition of 100 µL of a solution of disodium paranitrophenylphosphate (PnPP) (Sigma) at 1 mg/mL, in DEA-HCl buffer, to each well. After incubation for 20 min at ambient temperature, away from the light, the absorbance at 405 nm is measured using a plate reader (Multiskan MCC340 Wallace). The mice are regarded as seroconverted when the absorbance obtained is 2.5 times higher than the absorbance obtained with the negative control originating from serum from healthy naive mice (FIG. 10).

The vaccinated mice in batch (i) all display seroconversion, in contrast to the unvaccinated mice in batch (ii).

b) Isotypic Profile of the Anti-*N. caninum* IgGs

Figure 11:
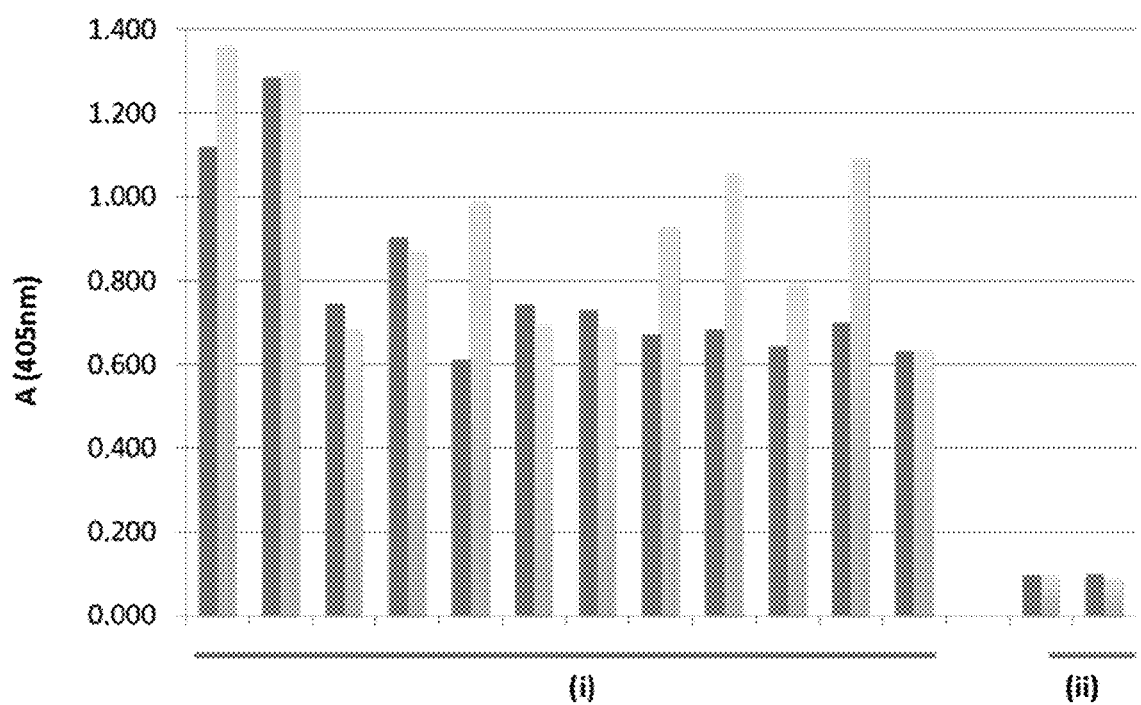

The total parasite extract of the strain NC-1 is diluted in a carbonate buffer pH9.6 in order to obtain a final concentration of 10 µg/mL. Flat-bottomed 96-well plates are then sensitized overnight at +4° C. by depositing 100 µL of total extract of *N. caninum* in each well. The plates are then washed three times with the washing buffer (1×PBS—0.05% TWEEN® 20) and then saturated for 1.5 h at 37° C. with a solution of 1×PBS—0.05% TWEEN® 20 supplemented with 4% of bovine serum albumin (BSA) (Sigma). The medium is then removed. The sera to be tested are diluted to 1/100th in a solution of 1×PBS—0.05% TWEEN® 20 and are deposited in duplicate in the wells. After incubation for 1 hour at 37° C. and a new series of washings, the secondary antibodies are deposited. The anti-IgG1 secondary antibodies (BD 557272, rat anti-Mouse IgG1) and anti-IgG2a secondary antibodies (BD 553389, rat anti-Mouse IgG2a) coupled to alkaline phosphatase and diluted to 1/1000th are deposited at a rate of 100 µL per well. The samples are then incubated for one hour at 37° C. After a new series of three washings, the detection is carried out by the addition of 100 µL of a solution of disodium paranitrophenylphosphate (PnPP) (Sigma) at 1 mg/mL, in DEA-HCl buffer, to each well. After incubation for 20 min at ambient temperature, away from the light, the absorbance at 405 nm is measured using a plate reader (Multiskan MCC340 Wallace) (FIG. 11).

The anti-*N. caninum* IgGs of the vaccinated mice in batch (i) are preferably of type IgG2A, an isotypic profile favourable to protection against *Neospora caninum* (Long et al., *J. Parasitol.*, 1998, April; 84(2): 316-20).

Example 9

Efficacy of the Mutant Strain Neo Mic1-3 KO in the Prevention of Neosporosis in a Murine Model of Congenital Neosporosis—Experiment 2

The mutant strain Neo ncmic1-3 KO described in Example 3 was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

Female OF1 mice were divided into 2 separate batches: (i) a batch of 11 mice vaccinated by intraperitoneal route with $5\cdot10^7$ tachyzoites of the mutant strain Neo ncmic1-3 KO and (ii) a batch of 6 unvaccinated control mice.

Two months after vaccination, the mice were mated (D0) at a rate of three female mice to one male. The pregnant mice in batches (i) and (ii) are diagnosed by weighing and on the tenth day of gestation are subjected to infectious challenge by intraperitoneal route with $2\times10^6$ tachyzoites of the wild-type strain NC1 of *Neospora caninum*. The wild-type strain NC1 of *Neospora caninum* was maintained by regular passages on HFF cells cultured in DMEM medium supplemented with 10% of foetal calf serum (FCS), 2 mM of glutamine, 50 U/mL of penicillin and 50 µg/mL of streptomycin. As the passages on HFF cells reduce the virulence of the parasites (Baszler et al., *Clin. Diagn. Lab. Immunol.*, 2000, November; 7(6)893-898 and Bartley et al., *Parasitology*, 2006, October; 133(4): 421-32), the number of passages on HFF cells is deliberately limited to 20.

One day before parturition, the female mice were sacrificed. The placentas and the foetuses were isolated and the DNA was extracted. A nested PCR is carried out from the region of the NC5 gene of *N. caninum* (Yamage et al., J. Parasitol. 1996 April 82(2): 272-9, Baszler et al., J Clin Microbiol, 1999 December, 37(12): 4059-64). The primer pair NC5 FA (SEQ ID NO: 31) and NC5 RA (SEQ ID NO: 32) is used for the primary PCR, and the primer pair NC5 FB (SEQ ID NO: 33) and NC5 RB (SEQ ID NO: 34) is used for the secondary PCR. The sequences of the primers are given in Table XI below.

TABLE XI

List of the primers used for the PCRs for investigating for the presence of the parasite *N. caninum* in the tissues.

| Name of the primer | 5'→3' Sequence | No. of sequence | No. of PCR |
|---|---|---|---|
| NC5 FA | CCCAGTGCGTCCAA TCCTGTAAC | SEQ ID NO: 31 | Primary |
| NC5 RA | CTCGCCAGTCAACC TACGTCTTCT | SEQ ID NO: 32 | Primary |
| NC5 FB | TAATCTCCCCCGTC ATCAGT | SEQ ID NO: 33 | Secondary |
| NC5 RB | GGGTGAACCGAGGG AGTTG | SEQ ID NO: 34 | Secondary |

For each placenta and foetus, three independent PCRs are carried out. The placentas and foetuses are considered positive when *Neospora caninum* is detected in the case of at least one PCR. The results are presented in Table XII below.

TABLE XII

Investigation for *Neospora caninum* in the placental and foetal tissues of mice vaccinated with the strain Neo ncmic1-3 KO and challenged with the wild-type strain NC1 (batch (i)) in comparison with unvaccinated control mice, challenged with the wild-type strain NC1 (batch (ii)).

| Batch (i) Mice vaccinated with $5 \cdot 10^7$ tachyzoites of the strain Neo ncmic1-3 KO and challenged with $2 \cdot 10^6$ tachyzoites of the wild-type strain NC1 | Investigation for *Neospora caninum* in the placentas | | |
|---|---|---|---|
| | Number of placentas investigated | Number of positive placentas | % of positive placentas |
| | 131 | 15 | 11.4% |
| | Investigation for *Neospora caninum* in the foetuses | | |
| | Number of foetuses investigated | Number of positive foetuses | % of positive foetuses |
| | 142 | 7 | 4.93% |
| Batch (ii) Unvaccinated mice, challenged with $2 \cdot 10^6$ tachyzoites of the wild-type strain NC1 | Investigation for *Neospora caninum* in the placentas | | |
| | Number of placentas investigated | Number of positive placentas | % of positive placentas |
| | 88 | 82 | 93.2% |
| | Investigation for *Neospora caninum* in the foetuses | | |
| | Number of foetuses investigated | Number of positive foetuses | % of positive foetuses |
| | 87 | 52 | 59.8% |

These results demonstrate that vaccination with the attenuated mutant strain Neo ncmic1-3 KO reduces the maternal-foetal transmission of the parasite considerably, thus validating the efficacy of the strain Neo mic1-3 KO for preventing harmful effects of neosporosis in a murine model of endogenous congenital neosporosis.

Example 10

Efficacy of the Mutant Strain Neo Ncmic1-3 KO in the Prevention of Neosporosis in a Murine Model of Congenital Neosporosis after Infection of the Mothers Prior to Gestation The mutant strain Neo ncmic1-3 KO described in Example 3 was maintained by regular passages on HFF cells cultured in DMEM medium supplemented with 10% of foetal calf serum (FCS); 2 mM of glutamine, 50 U/mL of penicillin and 50 µg/mL of streptomycin. As the passages on HFF cells reduce the virulence of the parasites (Baszler et al., Clin. Diagn. Lab. Immunol., 2000 November; 7(6)893-898 and Bartley et al., Parasitology, 2006, October; 133(4): 421-32), the number of passages on HFF cells is deliberately limited to 20.

Female OF1 mice were divided into 3 separate batches:

Batch (i): control batch comprising 9 mice infected by intraperitoneal route with $5 \cdot 10^6$ tachyzoites of the strain NC-1, Batch (ii): batch comprising 9 mice infected by intraperitoneal route with $5 \cdot 10^6$ tachyzoites of the wild-type strain NC-1 and then vaccinated 58 days later with $5 \cdot 10^7$ tachyzoites of the strain Neo ncmic1-3 KO by intraperitoneal route, Batch (iii): batch comprising 9 mice vaccinated by intraperitoneal route with $5 \cdot 10^7$ tachyzoites of the strain Neo ncmic1-3 KO and then infected, 58 days later, by intraperitoneal route with $5 \cdot 10^6$ tachyzoites of the wild-type strain NC-1.

One hundred and seven days after the start of the experiments, the mice were mated at a rate of 3 female mice to one male. The pregnant mice are diagnosed by weighing.

At 18 days of gestation, i.e. one day before theoretical parturition, the female mice are sacrificed. The foetuses are isolated and the DNA is extracted.

A nested PCR is carried out from the region of the NC5 gene of *N. caninum* (Yamage et al., J. Parasitol, 1996 April, 82(2): 272-9, Baszler et al., J. Clin. Microbiol, 1999 December, 37(12): 4059-64). The primer pair NC5 FA (SEQ ID NO: 31) and NC5 RA (SEQ ID NO: 32) is used for the primary PCR, and the primer pair NC5 FB (SEQ ID NO: 33) and NC5 RB (SEQ ID NO: 34) is used for the secondary PCR. The sequences of the primers are given in Table XIII below.

TABLE XIII

List of the primers used for the PCRs for investigating for the presence of the parasite *N. caninum* in the tissues.

| Name of the primer | 5'→3' Sequence | No. of sequence | No. of PCR |
|---|---|---|---|
| NC5 FA | CCCAGTGCGTCCAATCC TGTAAC | SEQ ID NO: 31 | Primary |
| NC5 RA | CTCGCCAGTCAACCTAC GTCTTCT | SEQ ID NO: 32 | Primary |
| NC5 FB | TAATCTCCCCCGTCATC AGT | SEQ ID NO: 33 | Secondary |
| NC5 RB | GGGTGAACCGAGGGAGT TG | SEQ ID NO: 34 | Secondary |

For each foetus, 3 independent PCRs are carried out. The foetus is regarded as positive when *Neospora caninum* is detected in the case of at least one PCR. The results are presented in Table XIV below.

TABLE XIV

Investigation for *Neospora caninum* in the placental and foetal tissues of mouse pups from mothers infected before gestation (Batch (i)), from mothers infected and then vaccinated before gestation (Batch (ii)) and from mothers vaccinated and then infected before gestation (Batch (iii)).

| Batch (i) 9 female mice infected with $5.10^6$ tachyzoites of the wild-type strain NC1 before being mated | Investigation for *Neospora caninum* in the placentas | | |
|---|---|---|---|
| | Number of placentas investigated | Number of positive placentas | % of positive placentas |
| | 96 | 28 | 29.2% |
| | Investigation for *Neospora caninum* in the foetuses | | |
| | Number of foetuses investigated | Number of positive foetuses | % of positive foetuses |
| | 97 | 32 | 33% |
| Batch (ii) 9 female mice infected with $5.10^6$ tachyzoites of the wild-type strain NC1 and then vaccinated with 5.107 tachyzoites of the strain Neo mic1-3 KO before being mated | Investigation for *Neospora caninum* in the placentas | | |
| | Number of placentas investigated | Number of positive placentas | % of positive placentas |
| | 110 | 13 | 11.81% |
| | Investigation for *Neospora caninum* in the foetuses | | |
| | Number of foetuses investigated | Number of positive foetuses | % of positive foetuses |
| | 113 | 15 | 13.27% |
| Batch (iii) 9 female mice vaccinated with $5.10^7$ tachyzoites of the strain Neo mic1-3 KO and then infected with $5.10^6$ tachyzoites of the wild-type strain NC1 before being mated | Investigation for *Neospora caninum* in the placentas | | |
| | Number of placentas investigated | Number of positive placentas | % of positive placentas |
| | 88 | 20 | 22.72% |
| | Investigation for *Neospora caninum* in the foetuses | | |
| | Number of foetuses investigated | Number of positive foetuses | % of positive foetuses |
| | 88 | 13 | 14.7% |

These results demonstrate that vaccination with the attenuated mutant strain Neo ncmic1-3 KO significantly reduces (Chi2 test, p<0.05) the maternal-foetal transmission of the parasite when the mothers are infected before gestation, thus validating the prophylactic and therapeutic efficacy of the strain Neo ncmic1-3 KO for preventing harmful effects of neosporosis in a murine model of congenital neosporosis with infection of the mother before gestation.

Example 11

Diagnostic Test for Differentiating the Vaccine Strain Neo Mic1-3 KO from the Wild-Type Strain NC1 after Injection in Mice The mutant strain Neo ncmic1-3 KO described in Example 3 was maintained by regular passages on HFF cells cultured in DMEM medium supplemented with 10% of foetal calf serum (FCS); 2 mM of glutamine, 50 U/mL of penicillin and 50 µg/mL of streptomycin. As the passages on HFF cells reduce the virulence of the parasites (Baszler et al., Clin. Diagn. Lab. Immunol., 2000 November; 7(6)893-898 and Bartley et al., Parasitology, 2006, October; 133(4): 421-32), the number of passages on HFF cells is deliberately limited to 20.

Female Balb/C mice were divided into 2 separate batches:
a batch injected by intraperitoneal route with $5·10^7$ tachyzoites of the mutant strain Neo ncmic1-3 KO,
and a batch injected by intraperitoneal route with $10^7$ tachyzoites of the wild-type strain NC1 of *Neospora caninum*.

The mice were sacrificed. The brains of the mice are then removed and ground in RPMI medium using a Potter. A proportion of the ground material is then deposited on HFF cells in DMEM medium supplemented with 10% of foetal calf serum (FCS), 2 mM of glutamine, 50 U/mL of penicillin and 50 µg/mL of streptomycin. The parasites are then harvested and their genomic DNA is extracted.

Starting from the genomic DNA, PCRs were carried out for:
verifying the presence or absence of the ncmic3 gene with the set of PCR primers No. 1: ORF NCmic3 F (SEQ ID NO: 7) and ORF NCmic3 R (SEQ ID NO: 8).
verifying the presence or absence of the DHFR cassette with the set of PCR primers No. 2: ORF DHFR F (SEQ ID NO: 9) and ORF DHFR R (SEQ ID NO: 10).
verifying the presence or absence of the ncmic1 gene with the set of PCR primers No. 3: stop Ncmic1 (SEQ ID NO: 39) and ORF NCmic1 R (SEQ ID NO: 25).
verifying the presence or absence of the CATGFP cassette with the set of PCR primers No. 4: ORF CATGFP F3 (SEQ ID NO: 49) and stop CATGFP (SEQ ID NO: 42).

The sequences of the primers and the size of the amplicons originating from the different PCRs are shown in Tables XVI and XVII below, respectively.

TABLE XVI

List of the primers used for diagnosing the mice vaccinated with the strain Neo ncmic1-3 KO and the mice infected with the strain NC-1 of *N. caninum*.

| Name of the primer | 5'→3' Sequence | No. of sequence | No. of PCR |
|---|---|---|---|
| ORF NCmic3 F | TTTCCCTTCTAAAC ACAGTCG | SEQ ID NO: 7 | 1 |
| ORF NCmic3 R | CCTTCAGTGGTTCT CCATGAGT | SEQ ID NO: 8 | 1 |
| ORF DHFR F | CCTTCTCAGACAAC GGGGTA | SEQ ID NO: 9 | 2 |
| ORF DHFR R | AGATCTTCACGCCC TTCTCA | SEQ ID NO: 10 | 2 |
| stop Ncmic1 | TTACAATTCAGATT CACCCG | SEQ ID NO: 39 | 3 |
| ORF NCmic1 R | TTCTCCAGGCACTC ACCT | SEQ ID NO: 25 | 3 |
| ORF CATGFP F3 | TTCATCATGCCGTT TGTGAT | SEQ ID NO: 49 | 4 |
| stop CATGFP | TTAATCGAGCGGGT CCTGGT | SEQ ID NO: 42 | 4 |

TABLE XVII

Size of the amplicons obtained in base pairs from the different PCRs for differential diagnosis between mice vaccinated with the strain Neo ncmic1-3 KO and the mice infected with the strain NC-1 of *N. caninum*.

| No. of PCR | Neo ncmic1-3 KO | *Neospora caninum* (NC-1) |
|---|---|---|
| 1 | — | 850 |
| 2 | 504 | — |
| 3 | — | 716 |
| 4 | 875 | — |

The amplicons obtained by PCR from samples originating from vaccinated mice and those obtained from samples originating from mice challenged with the strain NC-1 (FIG. 14) comply with the expected profiles and demonstrate:
absence of the ncmic3 and ncmic1 genes and presence of the DHFR and CATGFP cassettes in the case of the samples originating from mice vaccinated with the mutant strain Neo ncmic1-3 KO presence of the ncmic3 and ncmic1 genes and absence of the DHFR and CATGFP cassettes in the case of the samples originating from mice infected with the strain NC-1 of *N. caninum*.

These results confirm that it is possible to differentiate the vaccinated animals from the infected animals.

The invention claimed is:

1. A mutant strain of *Neospora canimum*, in which *Neospora* microneme 1 gene (nmic1 gene) and *Neospora* microneme 3 gene (nmic3 gene) are completely deleted, resulting in suppression of function of *Neospora* microneme 1 protein (NMIC1 protein) and function of *Neospora* microneme 3 protein (NMIC3 protein).

2. A pharmaceutical composition comprising the mutant strain according to claim 1 and a pharmaceutically acceptable vehicle.

3. The pharmaceutical composition according to claim 2, comprising a unit dose varying from $10^2$ to $10^9$ tachyzoites of the mutant strain.

4. A vaccine composition comprising a mutant strain as defined according to claim 1 and a pharmaceutically acceptable vehicle for the treatment of neosporosis in pet animals selected from the group consisting of dogs, horses and farm animals selected from the group consisting of ovines, caprines, bovines, porcines, camelids and cervids.

* * * * *

```
                            SEQUENCE LISTING

<160> NUMBER OF SEQ ID NOS: 49

<210> SEQ ID NO 1
<211> LENGTH: 34
<212> TYPE: DNA
<213> ORGANISM: Artificial Sequence
<220> FEATURE:
<223> OTHER INFORMATION: 5 HR NCmic3 F KpnI

<400> SEQUENCE: 1
cgcggtaccc atgtgaatat gctttaaccg tgac                               34

<210> SEQ ID NO 2
<211> LENGTH: 34
<212> TYPE: DNA
<213> ORGANISM: Artificial Sequence
<220> FEATURE:
<223> OTHER INFORMATION: 5 HR NCmic3 R ClaI

<400> SEQUENCE: 2
cgcatcgatg agctataacc cttggaaatg actc                               34

<210> SEQ ID NO 3
<211> LENGTH: 31
<212> TYPE: DNA
<213> ORGANISM: Artificial Sequence
<220> FEATURE:
<223> OTHER INFORMATION: 3 HR NCmic3 F XbaI

<400> SEQUENCE: 3
cgctctagac atgctgatga agaagggaag t                                  31

<210> SEQ ID NO 4
<211> LENGTH: 34
<212> TYPE: DNA
<213> ORGANISM: Artificial Sequence
<220> FEATURE:
<223> OTHER INFORMATION: 3 HR NCmic3 R NotI

<400> SEQUENCE: 4
cgcgcggccg ctctctcctg aagtcttcga gacc                               34

<210> SEQ ID NO 5
<211> LENGTH: 25
<212> TYPE: DNA
<213> ORGANISM: Artificial Sequence
<220> FEATURE:
<223> OTHER INFORMATION: HR NCmic3 F

<400> SEQUENCE: 5
gtcatcgacc gccggaacta gtagt                                         25

<210> SEQ ID NO 6
<211> LENGTH: 26
<212> TYPE: DNA
<213> ORGANISM: Artificial Sequence
<220> FEATURE:
<223> OTHER INFORMATION: HR NCmic3 R

<400> SEQUENCE: 6
```

-continued gcagaggttc tgcgtatcta acacgg    26

<210> SEQ ID NO 7
<211> LENGTH: 21
<212> TYPE: DNA
<213> ORGANISM: Artificial Sequence
<220> FEATURE:
<223> OTHER INFORMATION: ORF NCmic3 F

<400> SEQUENCE: 7
tttcccttct aaacacagtc g    21

<210> SEQ ID NO 8
<211> LENGTH: 22
<212> TYPE: DNA
<213> ORGANISM: Artificial Sequence
<220> FEATURE:
<223> OTHER INFORMATION: ORF NCmic3 R

<400> SEQUENCE: 8
ccttcagtgg ttctccatga gt    22

<210> SEQ ID NO 9
<211> LENGTH: 20
<212> TYPE: DNA
<213> ORGANISM: Artificial Sequence
<220> FEATURE:
<223> OTHER INFORMATION: ORF DHFR F

<400> SEQUENCE: 9
ccttctcaga caacggggta    20

<210> SEQ ID NO 10
<211> LENGTH: 20
<212> TYPE: DNA
<213> ORGANISM: Artificial Sequence
<220> FEATURE:
<223> OTHER INFORMATION: ORF DHFR R

<400> SEQUENCE: 10
agatcttcac gcccttctca    20

<210> SEQ ID NO 11
<211> LENGTH: 24
<212> TYPE: DNA
<213> ORGANISM: Artificial Sequence
<220> FEATURE:
<223> OTHER INFORMATION: Integ NCmic3 F

<400> SEQUENCE: 11
gaaagtgtca gtggtagaga ctgc    24

<210> SEQ ID NO 12
<211> LENGTH: 27
<212> TYPE: DNA
<213> ORGANISM: Artificial Sequence
<220> FEATURE:
<223> OTHER INFORMATION: ORF NCmic3 R2

<400> SEQUENCE: 12
ccttcactcg agatcgcgca aatgagc    27

<210> SEQ ID NO 13
<211> LENGTH: 23
<212> TYPE: DNA

```
<213> ORGANISM: Artificial Sequence
<220> FEATURE:
<223> OTHER INFORMATION: ORF DHFR R2

<400> SEQUENCE: 13
ggacctctgt acgagacatg ccg                                            23

<210> SEQ ID NO 14
<211> LENGTH: 24
<212> TYPE: DNA
<213> ORGANISM: Artificial Sequence
<220> FEATURE:
<223> OTHER INFORMATION: Integ NCmic3 R

<400> SEQUENCE: 14
tgtttacagg tgatccagaa aagg                                           24

<210> SEQ ID NO 15
<211> LENGTH: 20
<212> TYPE: DNA
<213> ORGANISM: Artificial Sequence
<220> FEATURE:
<223> OTHER INFORMATION: ORF NCmic3 F2

<400> SEQUENCE: 15
gaattttggg acagggggaat                                               20

<210> SEQ ID NO 16
<211> LENGTH: 25
<212> TYPE: DNA
<213> ORGANISM: Artificial Sequence
<220> FEATURE:
<223> OTHER INFORMATION: ORF DHFR F2

<400> SEQUENCE: 16
gtctctcgtt ttcctctctt ttcgg                                          25

<210> SEQ ID NO 17
<211> LENGTH: 33
<212> TYPE: DNA
<213> ORGANISM: Artificial Sequence
<220> FEATURE:
<223> OTHER INFORMATION: 3 HR NCmic1 F KpnI

<400> SEQUENCE: 17
cgcggtacca ggcagaagta aagaaggttc ctc                                 33

<210> SEQ ID NO 18
<211> LENGTH: 30
<212> TYPE: DNA
<213> ORGANISM: Artificial Sequence
<220> FEATURE:
<223> OTHER INFORMATION: 3 HR NCmic1 R HindIII

<400> SEQUENCE: 18
cgcaagcttt gatcacgcaa gaaaagaagc                                     30

<210> SEQ ID NO 19
<211> LENGTH: 32
<212> TYPE: DNA
<213> ORGANISM: Artificial Sequence
<220> FEATURE:
<223> OTHER INFORMATION: 5 HR NCmic1 F BamHI

<400> SEQUENCE: 19
cgcggatccc atttgtagat acggttgcac ac                                  32
```

<210> SEQ ID NO 20
<211> LENGTH: 33
<212> TYPE: DNA
<213> ORGANISM: Artificial Sequence
<220> FEATURE:
<223> OTHER INFORMATION: 5 HR NCmic1 R NotI

<400> SEQUENCE: 20
cgcgcggccg cacattcaga cggcagaact ctg                            33

<210> SEQ ID NO 21
<211> LENGTH: 20
<212> TYPE: DNA
<213> ORGANISM: Artificial Sequence
<220> FEATURE:
<223> OTHER INFORMATION: Integ NCmic1 F

<400> SEQUENCE: 21
ccgagcaagt tagcaagtcc                                           20

<210> SEQ ID NO 22
<211> LENGTH: 20
<212> TYPE: DNA
<213> ORGANISM: Artificial Sequence
<220> FEATURE:
<223> OTHER INFORMATION: ORF CATGFP R

<400> SEQUENCE: 22
ccgtttggtg gatgtcttct                                           20

<210> SEQ ID NO 23
<211> LENGTH: 20
<212> TYPE: DNA
<213> ORGANISM: Artificial Sequence
<220> FEATURE:
<223> OTHER INFORMATION: ORF CATGFP F

<400> SEQUENCE: 23
gcatcgactt caaggaggac                                           20

<210> SEQ ID NO 24
<211> LENGTH: 20
<212> TYPE: DNA
<213> ORGANISM: Artificial Sequence
<220> FEATURE:
<223> OTHER INFORMATION: Integ NCmic1 R

<400> SEQUENCE: 24
cttgtccgtc acatcgtttg                                           20

<210> SEQ ID NO 25
<211> LENGTH: 20
<212> TYPE: DNA
<213> ORGANISM: Artificial Sequence
<220> FEATURE:
<223> OTHER INFORMATION: ORF NCmic1 R

<400> SEQUENCE: 25
ttctccaggc actcacctct                                           20

<210> SEQ ID NO 26
<211> LENGTH: 20
<212> TYPE: DNA
<213> ORGANISM: Artificial Sequence
<220> FEATURE:

<223> OTHER INFORMATION: ORF NCmic1 F

<400> SEQUENCE: 26
agcttccaac aacgagagga					20

<210> SEQ ID NO 27
<211> LENGTH: 20
<212> TYPE: DNA
<213> ORGANISM: Artificial Sequence
<220> FEATURE:
<223> OTHER INFORMATION: ORF NCmic1 F2

<400> SEQUENCE: 27
cccaggatat cgtttgttgc					20

<210> SEQ ID NO 28
<211> LENGTH: 20
<212> TYPE: DNA
<213> ORGANISM: Artificial Sequence
<220> FEATURE:
<223> OTHER INFORMATION: ORF NCmic1 R2

<400> SEQUENCE: 28
cttctgatgc acggaactga					20

<210> SEQ ID NO 29
<211> LENGTH: 20
<212> TYPE: DNA
<213> ORGANISM: Artificial Sequence
<220> FEATURE:
<223> OTHER INFORMATION: ORF CATGFP F2

<400> SEQUENCE: 29
cctgaagttc atctgcacca					20

<210> SEQ ID NO 30
<211> LENGTH: 20
<212> TYPE: DNA
<213> ORGANISM: Artificial Sequence
<220> FEATURE:
<223> OTHER INFORMATION: ORFCATGFP R2

<400> SEQUENCE: 30
gtagtggttg tcgggcagca					20

<210> SEQ ID NO 31
<211> LENGTH: 23
<212> TYPE: DNA
<213> ORGANISM: Artificial Sequence
<220> FEATURE:
<223> OTHER INFORMATION: NC5 FA

<400> SEQUENCE: 31
cccagtgcgt ccaatcctgt aac				23

<210> SEQ ID NO 32
<211> LENGTH: 24
<212> TYPE: DNA
<213> ORGANISM: Artificial Sequence
<220> FEATURE:
<223> OTHER INFORMATION: NC5 RA

<400> SEQUENCE: 32
ctcgccagtc aacctacgtc ttct				24

```
<210> SEQ ID NO 33
<211> LENGTH: 20
<212> TYPE: DNA
<213> ORGANISM: Artificial Sequence
<220> FEATURE:
<223> OTHER INFORMATION: NC5 FB

<400> SEQUENCE: 33
taatctcccc cgtcatcagt                                               20

<210> SEQ ID NO 34
<211> LENGTH: 19
<212> TYPE: DNA
<213> ORGANISM: Artificial Sequence
<220> FEATURE:
<223> OTHER INFORMATION: NC5 RB

<400> SEQUENCE: 34
gggtgaaccg agggagttg                                                19

<210> SEQ ID NO 35
<211> LENGTH: 20
<212> TYPE: DNA
<213> ORGANISM: Artificial Sequence
<220> FEATURE:
<223> OTHER INFORMATION: ATG Ncmic1

<400> SEQUENCE: 35
atgggccagt cggtggtttt                                               20

<210> SEQ ID NO 36
<211> LENGTH: 20
<212> TYPE: DNA
<213> ORGANISM: Artificial Sequence
<220> FEATURE:
<223> OTHER INFORMATION: ATG Ncmic3

<400> SEQUENCE: 36
atgcgtggcg gggcgtccgc                                               20

<210> SEQ ID NO 37
<211> LENGTH: 19
<212> TYPE: DNA
<213> ORGANISM: Artificial Sequence
<220> FEATURE:
<223> OTHER INFORMATION: ATG DHFR

<400> SEQUENCE: 37
atgcagaaac cggtgtgtc                                                19

<210> SEQ ID NO 38
<211> LENGTH: 22
<212> TYPE: DNA
<213> ORGANISM: Artificial Sequence
<220> FEATURE:
<223> OTHER INFORMATION: ATG CATGFP

<400> SEQUENCE: 38
atgcatgaga aaaaaatcac tg                                            22

<210> SEQ ID NO 39
<211> LENGTH: 20
<212> TYPE: DNA
<213> ORGANISM: Artificial Sequence
<220> FEATURE:
<223> OTHER INFORMATION: stop Ncmic1
```

<400> SEQUENCE: 39
ttacaattca gattcacccg                                            20

<210> SEQ ID NO 40
<211> LENGTH: 22
<212> TYPE: DNA
<213> ORGANISM: Artificial Sequence
<220> FEATURE:
<223> OTHER INFORMATION: stop Ncmic3

<400> SEQUENCE: 40
ttatcgagcc gttccgcatt tg                                         22

<210> SEQ ID NO 41
<211> LENGTH: 21
<212> TYPE: DNA
<213> ORGANISM: Artificial Sequence
<220> FEATURE:
<223> OTHER INFORMATION: stop DHFR

<400> SEQUENCE: 41
ctagacagcc atctccatct g                                          21

<210> SEQ ID NO 42
<211> LENGTH: 20
<212> TYPE: DNA
<213> ORGANISM: Artificial Sequence
<220> FEATURE:
<223> OTHER INFORMATION: stop CATGFP

<400> SEQUENCE: 42
ttaatcgagc gggtcctggt                                            20

<210> SEQ ID NO 43
<211> LENGTH: 21
<212> TYPE: DNA
<213> ORGANISM: Artificial Sequence
<220> FEATURE:
<223> OTHER INFORMATION: Olig 1

<400> SEQUENCE: 43
cagatggaga tggctgtcta g                                          21

<210> SEQ ID NO 44
<211> LENGTH: 20
<212> TYPE: DNA
<213> ORGANISM: Artificial Sequence
<220> FEATURE:
<223> OTHER INFORMATION: Olig 2

<400> SEQUENCE: 44
cgctttcgtt ctgattgaca                                            20

<210> SEQ ID NO 45
<211> LENGTH: 20
<212> TYPE: DNA
<213> ORGANISM: Artificial Sequence
<220> FEATURE:
<223> OTHER INFORMATION: Olig 3

<400> SEQUENCE: 45
aaaaccaccg actggcccat                                            20

<210> SEQ ID NO 46
<211> LENGTH: 20

```
<212> TYPE: DNA
<213> ORGANISM: Artificial Sequence
<220> FEATURE:
<223> OTHER INFORMATION: Olig 4

<400> SEQUENCE: 46
tcctctcgtt gttggaagct                                          20

<210> SEQ ID NO 47
<211> LENGTH: 20
<212> TYPE: DNA
<213> ORGANISM: Artificial Sequence
<220> FEATURE:
<223> OTHER INFORMATION: Olig 5

<400> SEQUENCE: 47
tagcacggga aaggattgac                                          20

<210> SEQ ID NO 48
<211> LENGTH: 19
<212> TYPE: DNA
<213> ORGANISM: Artificial Sequence
<220> FEATURE:
<223> OTHER INFORMATION: Olig 6

<400> SEQUENCE: 48
caagatccgc cacaacatc                                           19

<210> SEQ ID NO 49
<211> LENGTH: 20
<212> TYPE: DNA
<213> ORGANISM: Artificial Sequence
<220> FEATURE:
<223> OTHER INFORMATION: ORF CATGFP F3

<400> SEQUENCE: 49
ttcatcatgc cgtttgtgat                                          20
```